(12) United States Patent
Farrer et al.

(10) Patent No.: US 8,622,546 B2
(45) Date of Patent: Jan. 7, 2014

(54) METHOD OF LOCATING VALID LIGHT SPOTS FOR OPTICAL MEASUREMENT AND OPTICAL MEASUREMENT INSTRUMENT EMPLOYING METHOD OF LOCATING VALID LIGHT SPOTS

(75) Inventors: Stephen W. Farrer, Albuquerque, NM (US); Thomas D. Raymond, Edgewood, NM (US); Wei Xiong, Albuquerque, NM (US); John Dixson, Albuquerque, NM (US); Daniel R. Neal, Tijeras, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 206 days.

(21) Appl. No.: 13/156,013

(22) Filed: Jun. 8, 2011

(65) Prior Publication Data

US 2012/0314187 A1 Dec. 13, 2012

(51) Int. Cl.
*A61B 3/00* (2006.01)
*A61B 3/10* (2006.01)

(52) U.S. Cl.
USPC .......................... 351/200; 351/221; 351/246

(58) Field of Classification Search
USPC ......................................... 351/200, 221, 246
See application file for complete search history.

(56) References Cited

U.S. PATENT DOCUMENTS

| | | | |
|---|---|---|---|
| 4,159,867 A | 7/1979 | Achatz et al. |
| 4,312,574 A | 1/1982 | Wilms |
| 4,420,228 A | 12/1983 | Humphrey |
| 4,440,477 A | 4/1984 | Schachar |
| 4,530,579 A | 7/1985 | Hyde |
| 4,569,576 A | 2/1986 | Karpov et al. |
| 4,588,270 A | 5/1986 | Tamaki |
| 4,662,730 A | 5/1987 | Outwater et al. |
| 4,666,269 A | 5/1987 | Nakamura et al. |
| 4,761,071 A | 8/1988 | Baron |
| 4,902,123 A | 2/1990 | Yoder, Jr. |
| 4,917,458 A | 4/1990 | Matsumura |
| 4,993,826 A | 2/1991 | Yoder, Jr. |
| 4,998,819 A | 3/1991 | Labinger et al. |

(Continued)

FOREIGN PATENT DOCUMENTS

| | | | |
|---|---|---|---|
| JP | 11164816 A | 6/1999 |
| MX | 1010791 A | 6/2003 |

(Continued)

OTHER PUBLICATIONS

International Search Report and Written Opinion for Application No. PCT/US2012/041085, mailed on Aug. 30, 2012, 12 pages.

(Continued)

*Primary Examiner* — Jack Dinh
(74) *Attorney, Agent, or Firm* — AMO Wavefront Sciences, LLC

(57) ABSTRACT

An algorithm locates valid light spots produced on an image detector by a wavefront of interest. The algorithm includes sequentially examining pixels of the image detector to determine for each of the pixels whether the light intensity detected by the pixel is greater than a threshold, When the pixel's detected light intensity is determined to be greater than the threshold, the algorithm includes: determining whether the pixel belongs to a valid light spot; and when the pixel is determined to belong to a valid light spot; saving data indicating a location for the valid light spot; and masking out a group of pixels of the image detector at the determined location such that the masked pixels are considered to have a light intensity less than the threshold for a remainder of the sequential examination.

18 Claims, 18 Drawing Sheets

(56) References Cited

U.S. PATENT DOCUMENTS

| | | |
|---|---|---|
| 5,054,907 A | 10/1991 | Sklar et al. |
| 5,062,702 A | 11/1991 | Bille |
| 5,106,183 A | 4/1992 | Yoder, Jr. |
| 5,110,200 A | 5/1992 | Snook |
| 5,283,598 A | 2/1994 | McMillan et al. |
| 5,349,398 A | 9/1994 | Koester |
| 5,392,079 A | 2/1995 | Fedorov et al. |
| 5,418,582 A | 5/1995 | van Saarloos |
| 5,585,873 A | 12/1996 | Shalon et al. |
| 5,640,962 A | 6/1997 | Jean et al. |
| 5,684,562 A | 11/1997 | Fujieda |
| 5,793,468 A | 8/1998 | Shalon et al. |
| 5,847,804 A | 12/1998 | Sarver et al. |
| 5,864,383 A | 1/1999 | Turner et al. |
| 5,873,832 A | 2/1999 | Maloney et al. |
| 5,886,767 A | 3/1999 | Snook |
| 5,909,270 A | 6/1999 | Moser et al. |
| 5,920,373 A | 7/1999 | Bille |
| 5,929,970 A | 7/1999 | Mihashi |
| 5,953,100 A | 9/1999 | Sarver et al. |
| 5,993,000 A | 11/1999 | Kobayashi et al. |
| 6,007,204 A | 12/1999 | Fahrenkrug et al. |
| 6,042,233 A | 3/2000 | Mihashi et al. |
| 6,048,065 A | 4/2000 | Davis et al. |
| 6,050,687 A | 4/2000 | Bille et al. |
| 6,059,773 A | 5/2000 | Maloney et al. |
| 6,079,831 A | 6/2000 | Sarver et al. |
| 6,086,204 A | 7/2000 | Magnante |
| 6,116,738 A | 9/2000 | Rorabaugh |
| 6,120,150 A | 9/2000 | Sarver et al. |
| 6,129,722 A | 10/2000 | Ruiz |
| 6,152,565 A | 11/2000 | Liu et al. |
| 6,234,631 B1 | 5/2001 | Sarver et al. |
| 6,234,632 B1 | 5/2001 | Nakao |
| 6,234,978 B1 | 5/2001 | Mihashi et al. |
| 6,257,723 B1 | 7/2001 | Sarver et al. |
| 6,271,914 B1 | 8/2001 | Frey et al. |
| 6,271,915 B1 | 8/2001 | Frey et al. |
| 6,299,309 B1 | 10/2001 | Ruiz |
| 6,305,802 B1 | 10/2001 | Roffman et al. |
| 6,379,008 B1 | 4/2002 | Chateau et al. |
| 6,382,795 B1 | 5/2002 | Lai |
| 6,394,605 B1 | 5/2002 | Campin et al. |
| 6,428,168 B2 | 8/2002 | Sarver et al. |
| 6,447,119 B1 | 9/2002 | Stewart et al. |
| 6,460,997 B1 | 10/2002 | Frey et al. |
| 6,467,907 B1 | 10/2002 | Fujieda et al. |
| 6,497,483 B2 | 12/2002 | Frey et al. |
| 6,511,179 B1 | 1/2003 | Davis et al. |
| 6,511,180 B2 | 1/2003 | Guirao et al. |
| 6,525,883 B2 | 2/2003 | Hirohara et al. |
| 6,540,692 B2 | 4/2003 | Mihashi et al. |
| 6,547,393 B2 | 4/2003 | Ruiz |
| 6,550,917 B1 | 4/2003 | Neal et al. |
| 6,565,209 B2 | 5/2003 | Campin |
| 6,569,154 B2 | 5/2003 | Campin et al. |
| 6,572,230 B2 | 6/2003 | Levine |
| 6,575,573 B2 | 6/2003 | Lai et al. |
| 6,592,574 B1 | 7/2003 | Shimmick et al. |
| 6,598,973 B2 | 7/2003 | Campin |
| 6,598,975 B2 | 7/2003 | Liang et al. |
| 6,601,956 B1 | 8/2003 | Jean et al. |
| 6,607,273 B2 | 8/2003 | Sarver et al. |
| 6,609,794 B2 | 8/2003 | Levine |
| 6,610,048 B1 | 8/2003 | Holladay et al. |
| 6,616,275 B1 | 9/2003 | Dick et al. |
| 6,629,761 B1 | 10/2003 | Hirohara et al. |
| 6,634,752 B2 | 10/2003 | Curatu |
| 6,637,884 B2 | 10/2003 | Martino |
| 6,666,857 B2 | 12/2003 | Smith |
| 6,685,320 B2 | 2/2004 | Hirohara et al. |
| 6,692,126 B1 | 2/2004 | Xie et al. |
| 6,695,450 B2 | 2/2004 | Hirohara et al. |
| 6,705,729 B2 | 3/2004 | Piers et al. |
| 6,739,721 B2 | 5/2004 | Altmann |
| 6,755,528 B2 | 6/2004 | Isogai |
| 6,808,266 B2 | 10/2004 | Youssefi |
| 6,827,444 B2 | 12/2004 | Williams et al. |
| 6,848,790 B1 | 2/2005 | Dick et al. |
| 6,905,209 B2 | 6/2005 | Mihashi et al. |
| 6,905,210 B2 | 6/2005 | Applegate et al. |
| 6,913,358 B2 | 7/2005 | Manuel Martins Borges De Almeida et al. |
| 6,926,408 B2 | 8/2005 | Sarver |
| RE38,839 E | 10/2005 | Magnante |
| 6,988,801 B2 | 1/2006 | Yoon |
| 7,029,119 B2 | 4/2006 | Youssefi et al. |
| 7,036,934 B1 | 5/2006 | Youssefi et al. |
| 7,044,603 B2 | 5/2006 | Yoon |
| 7,044,944 B2 | 5/2006 | Campin et al. |
| 7,122,774 B2 | 10/2006 | Topa |
| 7,146,983 B1 | 12/2006 | Hohla et al. |
| 7,216,980 B2 | 5/2007 | Mihashi et al. |
| 7,222,962 B2 | 5/2007 | Hirohara et al. |
| 7,226,443 B1 | 6/2007 | Campin et al. |
| 7,237,898 B1 | 7/2007 | Hohla et al. |
| 7,241,012 B2 | 7/2007 | Mihashi et al. |
| 7,249,851 B2 | 7/2007 | Hirohara et al. |
| RE39,882 E | 10/2007 | Mihashi et al. |
| 7,303,281 B2 | 12/2007 | Wakil et al. |
| 7,309,126 B2 | 12/2007 | Mihashi et al. |
| 7,325,927 B2 | 2/2008 | Applegate et al. |
| 7,394,595 B2 | 7/2008 | Somani et al. |
| 7,425,067 B2 | 9/2008 | Warden et al. |
| 7,494,220 B2 | 2/2009 | Copland |
| 2003/0063257 A1 | 4/2003 | Molebny |
| 2003/0169403 A1 | 9/2003 | Curatu |
| 2004/0021826 A1 | 2/2004 | Sarver et al. |
| 2004/0066489 A1 | 4/2004 | Benedikt et al. |
| 2004/0130705 A1 | 7/2004 | Topa |
| 2006/0152677 A1 | 7/2006 | Youssefi et al. |
| 2006/0209256 A1 | 9/2006 | Beyerlein et al. |
| 2007/0171365 A1 | 7/2007 | Tuan |
| 2008/0018910 A1 | 1/2008 | Neal et al. |
| 2009/0002631 A1 | 1/2009 | Campbell et al. |

FOREIGN PATENT DOCUMENTS

| | | |
|---|---|---|
| WO | WO0158339 A2 | 8/2001 |
| WO | WO03042649 A2 | 5/2003 |
| WO | WO03063695 A1 | 8/2003 |
| WO | WO03077740 A1 | 9/2003 |

OTHER PUBLICATIONS

International Search Report for Application No. PCT/US2009/064390, mailed on Jul. 15, 2010, 6 pages.

Liang J., et al, "Objective Measurement of Wave Aberrations of the Human Eye With the Use of a Hartmann-Shack Wave-Front Sensor," Journal of the Optical Society of America, 1994, vol. 11 (7), pp. 1949-1957.

Massig J.H., et al., "Videokeratoscope for Accurate and Detailed Measurement of the Cornea Surface," Optical Society of Americal, 2005, vol. 44 (12), pp. 2281-2287.

Mejia-Barbosa Y., "Correlation-Based Method for Comparing and Reconstructing Nearly Identical Two-Dimensional Structures," Applied Optics, 2001, vol. 40 (2), pp. 235-239.

Mejia-Barbosa Y., et al., "Object Surface for Applying a Modified Hartmann Test to Measure Corneal Topography," Applied Optics, 2001, vol. 40 (31), pp. 5778-5786.

Rubinstein J., et al., "Reconstruction of Optical Surfaces from Ray Data", Optical Review, pp. 281-283, 2001, vol. 8 (4).

Salmon T.O., et al., Corneal Contribution to the Wavefront Aberration of the Eye, University Graduate School, 1999.

Sicam V.A., et al., "Corneal Surface Reconstruction Algorithm that uses Zernike Polynomial Representation," Journal of Optical Society of America, 2004, vol. 21 (7), pp. 1300-1306.

Wang M., "Corneal Topography in the Wavefront Era: A Guide for Clinical Application" Slacker Incorporated, 1st edition, Chapter 4 Topographic Technologies; Mar. 1, 2006, pp. 31-40.

METHOD OF LOCATING VALID LIGHT SPOTS FOR OPTICAL MEASUREMENT AND OPTICAL MEASUREMENT INSTRUMENT EMPLOYING METHOD OF LOCATING VALID LIGHT SPOTS

BACKGROUND AND SUMMARY

1. Field

This invention pertains to devices and methods for performing optical measurements using a plurality of light spots, and more particularly, to a method of locating valid light spots for use in making optical measurements by a measurement instrument, and a measurement instrument employing such a method of locating the valid light spots that are employed in its measurements.

2. Description

There are some instruments which employ light spots to make optical measurements. Well-known examples include instruments which employ a Shack-Hartmann wave front sensor.

FIG. 1 illustrates some principal elements of a basic configuration of a Shack-Hartmann wavefront sensor 100. Shack-Hartmann wavefront sensor 100 comprises a micro-optic lenslet array 110 and an optical detector 120. Typically, the optical detector 120 comprises a detector array or pixel array, for example, a charge-coupled device (CCD) camera or CMOS array.

The lenslets of lenslet array 110 dissect an incoming wavefront and create a pattern of light spots 130 that fall onto optical detector 120. In one typical embodiment, lenslet array 110 includes hundreds or thousands of lenslets, each on the size scale of a hundred microns. Meanwhile, optical detector 120 typically comprises many pixels (e.g., about 400 pixels) for each lenslet in lenslet array 110. Typically Shack-Hartmann sensor 100 is assembled such that the pixel array 120 lies in the focal plane of lenslet array 110.

Shack-Hartmann wavefront sensor 100 uses the fact that light travels in a straight line to measure the wavefront of light. By sensing the locations of light spots 130, the propagation vector of the sampled light can be calculated for each lenslet of lenslet array 110. The wavefront of the received light can be reconstructed from these vectors.

To better understand one or more aspects of this invention, it is worthwhile to discuss the operation of Shack-Hartmann wavefront sensor 100 in more detail. However, embodiments of the present invention extend to other types of optical measurement devices and systems such as topographers. In certain embodiments of the present invention, a system includes two or more optical measurement devices, for example, a combined system including both a wavefront sensor and a topographer.

In the case of the wavefront sensor 100, some optical system is employed to deliver a wavefront onto the lenslet array 110, which samples the wavefront over the tiny regions of each lenslet. Beneficially, the lenslets are much smaller than the wavefront variation. For the purposes of this discussion, we define "isoplanatic" as the condition where the wavefront is well approximated by a plane wave over an area the size of a lenslet. In that case, the wavefront is preferably isoplanatic over the sampled region. When optical detector 120—hereafter referred to more specifically as "detector array 120"—is in the focal plane of lenslet array 110, each lenslet will create a light spot on detector array 120. The locations of these light spots reveal the average of the wavefront slopes across each region. That is, the shift in the location of a light spot is proportional to the average of the slope of the wavefront over the region sampled by the corresponding lenslet that produced the light spot. Software may compute the shift in each light spot.

In a typical operation, a reference beam (e.g., a plane wave) is first imaged onto lenslet array 110 and the locations of the resultant light spots ("reference locations") on detector array 120 is recorded. Then, a wavefront of interest is imaged onto lenslet array 110, and the locations of the light spots on detector array 120 produced by the wavefront of interest are recorded and compared against the reference locations.

FIGS. 2A-2E illustrate an idealized example of this process where a reference beam and a wavefront of interest are imaged onto a detector array of a wavefront sensor. This idealization shows the process of measuring a spherical wave with a wavefront sensor with just 16 lenslets.

The first step, as represented by the FIGS. 2A-2C, is to measure a plane wave and measure the corresponding series of light spot locations 210 which are used as reference locations 220. For the plane wave, each lenslet of lenslet array 110 produces one light spot on a location 210 within a corresponding Area of Interest (AOI) of pixel array 120 that lies beneath that lenslet.

The next step, as depicted in FIGS. 2D-2E, is to introduce a wavefront of interest and determine the shifts in the locations 240 of the light spots 230 from their reference locations 220.

Where the isoplanatic condition is satisfied and where the light spot shift is consistent with the small angle approximation of Fresnel, then the light spot shift is exactly proportional to the average of the wavefront slope over the lenslet. The incident wavefront is then reconstructed from the measurements of the average of the slopes for the hundreds or thousands of lenslets in the lenslet array.

Further details regarding the construction and operation of a Shack-Hartmann wavefront sensor and a system for measuring aberrations in an eye using the Shack-Hartman wavefront sensor are described in U.S. Pat. No. 7,122,774, issued on 17 Oct. 2006 to Daniel R. Neal et al., the entirety of which is hereby incorporated by reference for all purposes as if fully set forth herein.

One important application for Shack-Hartmann wavefront sensors is in the field of ophthalmic aberrometry. In common practice, a measurement instrument employing a Shack-Hartmann wavefront sensor injects near infrared light into a patient's eye which focuses on the retina and scatters back toward the instrument. This light is imaged onto the Shack-Hartmann lenslet array, and each lenslet in the lenslet array focuses the local portion of the incident light it intercepts onto the detector array, as described above. Data pertaining to the locations of the light spots is used to derive slope information using a least squares fit method, and thereby to construct the wavefront of the received light.

The nominally rectilinear array of light spots is produced by a rectilinear lenslet array. The detailed analysis of the locations of these light spots relative to their reference locations (i.e., the locations that result when a true plane wave is applied to the lenslet array) yields the local gradient of the incident wavefront. The overall area in which focal spots are present is determined by the patient's pupil, and analysis of this illuminated area yields the location size and shape of the pupil.

The application of Shack-Hartmann wavefront sensors to ophthalmic aberrometry has been a success.

However, the quality of the fit data, usually evaluated using Zernike coefficients, is affected by the quality of the light spot location data, and therefore it is important to ensure that the data quality is adequate to the measurement accuracy and precision requirements.

In particular, if the wavefront is not isoplanatic, the quality of the light spots erodes rapidly and it becomes more difficult to determine the locations of the light spots. More specifically, measuring highly aberrated light beams can lead to focal spot crossover such that light spot from a particular lenslets end up in locations on the pixel array that lie under neighboring lenslets, or end up in irregular locations not defined by a grid. As explained above with respect to FIGS. 2A-C, in a traditional system the first step to locating the light spots is to search in a predefined Area of Interest (AOI). However with a highly aberrated beam, there could be more than one light spot in an AOI, or an AOI for a particular pixel may include part of a light spot for a neighboring pixel. This will lead to errors in these traditional light spot location algorithms.

On method of dealing with this problem is the inclusion of a dynamic range limiting aperture in the measurement instrument to prevent to prevent light spots from appearing outside their AOIs on the detector array, as described for example in U.S. Pat. No. 6,550,917 issued on 22 Apr. 2003 to Daniel R. Neal et al., which is hereby incorporated by reference for all purposes as if fully set forth herein. The dynamic range limiting aperture clips portions of the light beam that impinge on the detector array above a certain angle. Accordingly, the dynamic range limiting aperture limits the dynamic range of the measurement instrument. So other methods of handling highly aberrated wavefronts are desired.

In addition to the problem of determining the locations of light spots for a highly aberrated light beam, in some cases lenslet array 110 may not be perfectly aligned with the pixels of detector array 120. That is, there may be a translational offset and/or a rotation angle between lenslet array 110 and detector array 120 that may complicate the wavefront analysis.

Additionally, there is a problem of determining what constitutes a valid light spot on the detector array.

FIG. 3 shows a typical raw image from a wavefront sensor. Some important error sources are illustrated in FIG. 3 and will be described below.

The incident near infrared beam not only scatters from a patient's retina, but also reflects directly from the patient's cornea. The use of a Range Limiting Aperture (RLA) in the measurement instrument, as described above, can significantly reduce the intensity of the reflected light. However, this so-called "corneal reflex" is generally orders of magnitude brighter than the desired retinally scattered light, and—beneficially—may be excluded from the wavefront calculations. Indeed, as is illustrated by reference numeral 310 in FIG. 3, the reflex can affect a neighborhood of nearby focal spots by introducing stray light that can alter the true light spot location or mask the light spot entirely. The location and intensity of the corneal reflex is affected by corneal shape and the actual position of the patient's eye when the data is acquired. For these reasons, the qualification and/or exclusion of light spot data in and around the corneal reflex can be challenging.

The retinal scatter that is necessary for the aberrometer measurement is highly speckled because the retinal structure is quite rough compared to the wavelength of the probe beam. This leads to variability in the relative brightness of the focal spots. A measurement instrument may employ a broadband probe beam to reduce the speckle, but even so, the intensity of the light spots can vary by a factor of four in a normal clear eye. Additional variation can be introduced by cataracts, "floaters" and opaque regions in pathological crystalline lenses. Cataracts diffuse the incident and return beams causing both reduced spot intensity and broader light spots. As a result, as shown in FIG. 3, the raw image from the wavefront sensor may include dim light spots 320 and/or missing light spots 330.

Additional reflections of the probe beam may be produced by each surface in eyes implanted with intraocular lenses (IOLs). While similar to the corneal reflex phenomenon, multiple reflections are typically present in these patients and may be far from the optic axis of the wavefront sensor. Also, in subjects with diffractive IOLs, it is expected that one lenslet focal spot per diffraction order transmitted through the optical system may be present. In some cases this will lead to two or more focal spots that may or may not be spatially separated. Such focal spot distributions can lead to inaccurate identification of the light spot location and therefore inaccurate wavefront measurements.

Another source of error in wavefront measurements is tear film breakup. Tear film break up can affect the location and sharpness of the light spots in the vicinity of the breakup. Tear film breakup is correlated to delays in blinking the eye. Some measurement systems may be designed to operate rapidly and reduce tear film breakup effects by avoiding the need to keep the patient from blinking for long periods. Nevertheless, it is still possible that light spots are affected by tear film breakup. This can negatively impact the resultant wavefront measurements.

The spot location algorithms used with a typical wavefront measurement instrument are designed to work with data taken within the nominal linear range of the detector device (e.g., a CMOS detector). It is apparent that the light spot location information is compromised when the spot brightness is poor compared to stray light and camera noise.

Therefore, it would be desirable to provide a method of locating valid light spots for use in optical measurements performed by a measurement instrument, particularly when measuring highly aberrated wavefronts. It would also be desirable to provide a measurement instrument employing a method of locating valid light spots for use in its optical measurements, particularly when measuring highly aberrated wavefronts. It would further be desirable to provide such a method and instrument that qualify light spots to verify their validity as part of the light spot location process.

In one aspect of the invention, a method is provided for locating a set of valid light spots produced on a pixel array by a wavefront of interest. The method includes a first stage and a second stage. The first stage comprises selecting a pixel of the pixel array. The second stage comprises: determining whether a light intensity value for the selected pixel is greater than a threshold, and when the light intensity value for the selected pixel is determined to be greater than the threshold, determining whether the selected pixel belongs to a valid light spot. The second stage further includes, when the selected pixel is determined to belong to a valid light spot, saving light spot location data indicating a determined location for the valid light spot with respect to the pixel array, and masking out a group of pixels of the pixel array corresponding to a defined area at the determined location of the valid light spot such that the masked pixels are considered for a remainder of the method to have light intensity values less than the threshold. The method further includes repeating the first stage and the second stage for a plurality of pixels of the pixel array.

Qualifying the set of light spots includes, for each light spot in the group of light spots: calculating a first calculated location of the light spot using a first calculation algorithm; calculating a second calculated location of the light spot using a second calculation algorithm different from the first calculation algorithm; and when a difference between the first and second calculated locations for the light spot is greater than an agreement threshold, excluding the light spot from the qualified set of light spots. In addition, the light spots excluded from the qualified set may be excluded from being employed in determining the property of the object.

In another aspect of the invention, a device includes: a pixel array; a light spot generator adapted to receive light from an illuminated objected and to produce a group of light spots on the pixel array from the light received from the illuminated object; and a processor adapted to determine locations of the light spots on the pixel array by executing an algorithm. The algorithm comprises: a first stage and a second stage. The first stage comprises selecting a pixel of the pixel array. The second stage comprises: determining whether a light intensity value for the selected pixel is greater than a threshold, and when the light intensity value for the selected pixel is determined to be greater than the threshold, determining whether the selected pixel belongs to one of the light spots. The second stage further includes, when the selected pixel is determined to belong to one of the light spots, saving light spot location data indicating a determined location for the one light spot with respect to the pixel array, and masking out a group of pixels of the pixel array corresponding to a defined area at the determined location of the one light spot such that the masked pixels are considered for a remainder of the algorithm to have light intensity values less than the threshold. The algorithm further includes repeating the first stage and the second stage for a plurality of pixels of the pixel array.

In yet another aspect of the invention, a method comprises: sequentially processing pixels of an image detector, wherein processing a pixel includes determining whether a light intensity detected by the pixel is greater than a threshold; when the light intensity detected by the pixel is determined to be greater than the threshold, and determining whether the pixel belongs to a valid light spot for measuring a wavefront of interest. The method further includes, when the pixel is determined to belong to a valid light spot, saving data indicating a location for the valid light spot, and masking out a group of pixels of the image detector at the location of the valid light spot such that the masked pixels are considered to have a light intensity less than the threshold for a remainder of the sequential processing of the pixels.

DETAILED DESCRIPTION

Methods and systems for locating valid light spot data as described below can be employed in a variety of different measurement instruments. Exemplary embodiments will be described in some detail below so as to illustrate various aspects and advantages of these methods. However, it should be understood that the principles involved in these method can be employed in a variety of other measurement instruments which employ light spot data.

Figure 4:
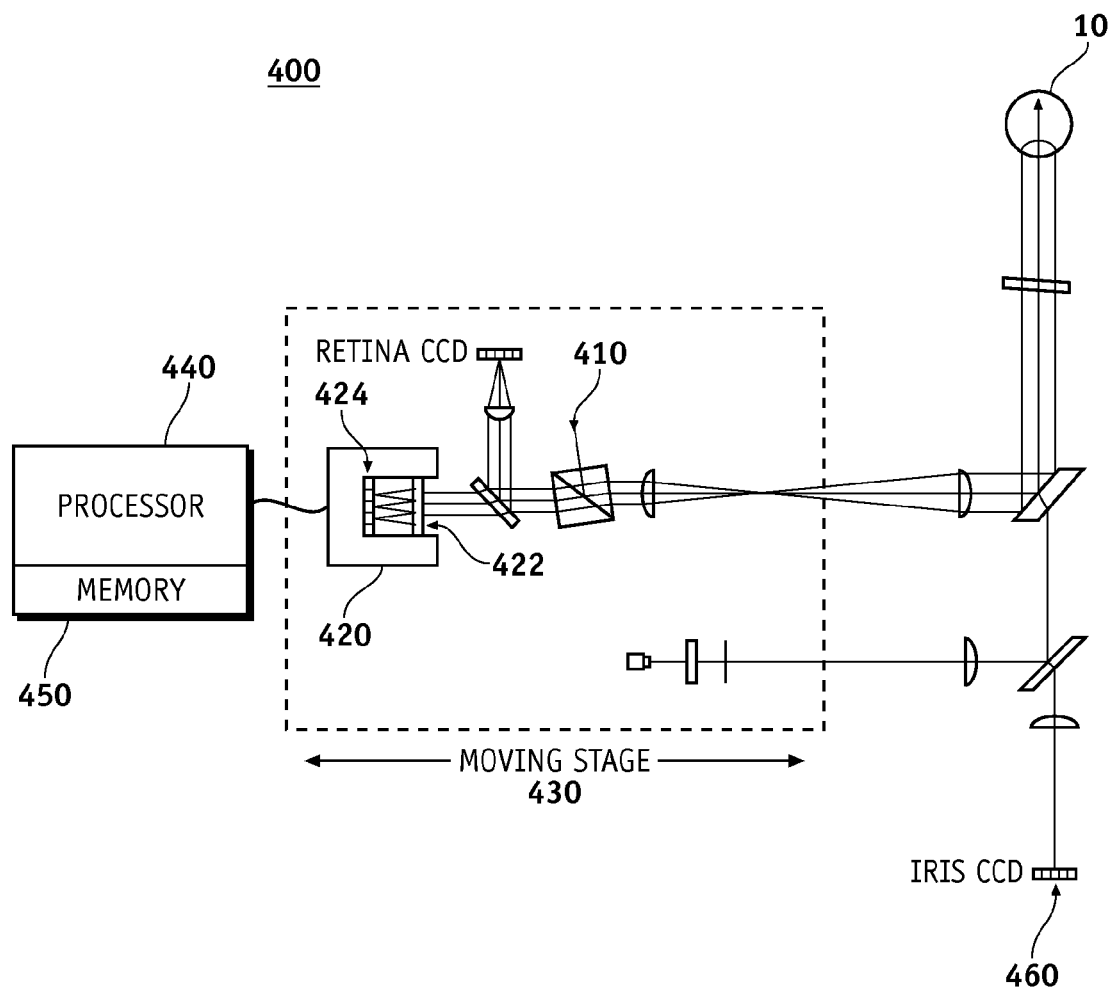
FIG. 4 illustrates one embodiment of a measurement instrument employing a wavefront sensor.

FIG. 4 illustrates one embodiment of a measurement instrument employing a wavefront sensor. In particular, FIG. 4 illustrates a wavefront aberrometer 400 for making wavefront measurements of a subject's eye 10. Among other components, wavefront aberrometer 400 includes a light source 410, a wavefront sensor 420, and other components on a moving stage 430, a processor 440, memory 450 associated with the processor 440, and an iris camera 460. Further details of the construction and operation of wavefront aberrometer 400 can be found in U.S. Pat. No. 7,494,220 issued on 24 Feb. 2009 in the names of Richard Copland et al., the entirety of which is hereby incorporated herein by reference for all purposes as if fully set forth herein.

Figure 1:
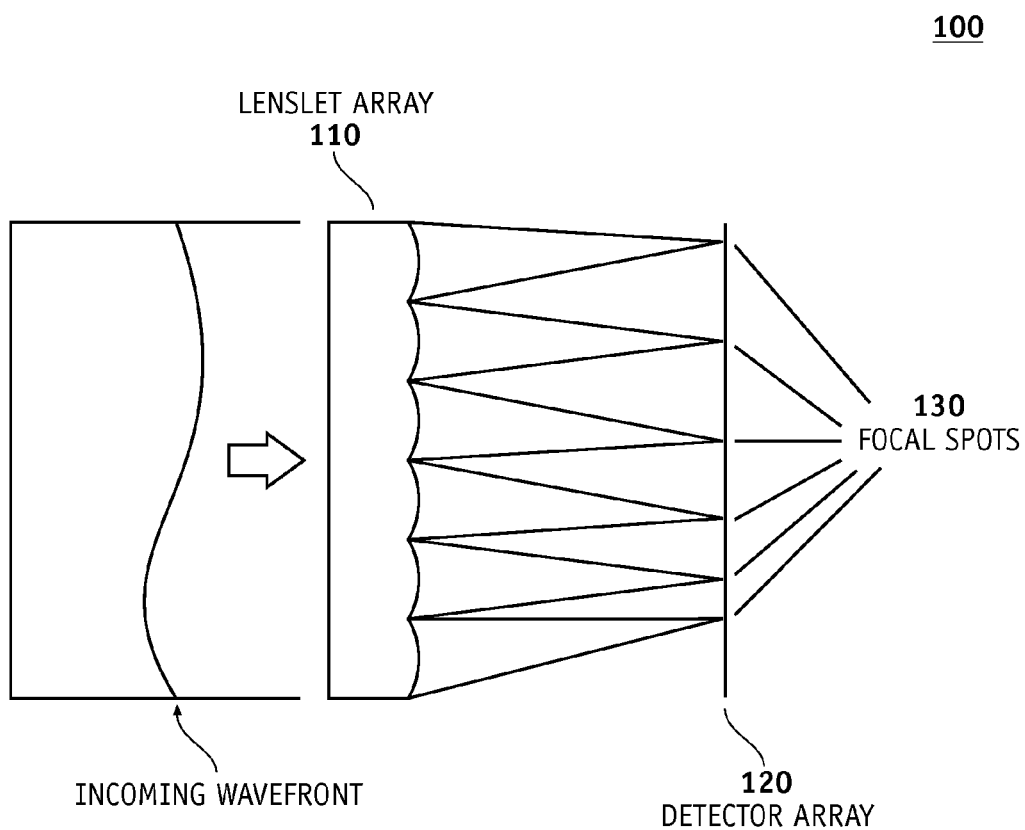
FIG. 1 illustrates some principal elements of a basic configuration of a Shack-Hartmann wavefront sensor.
Figure 2A:
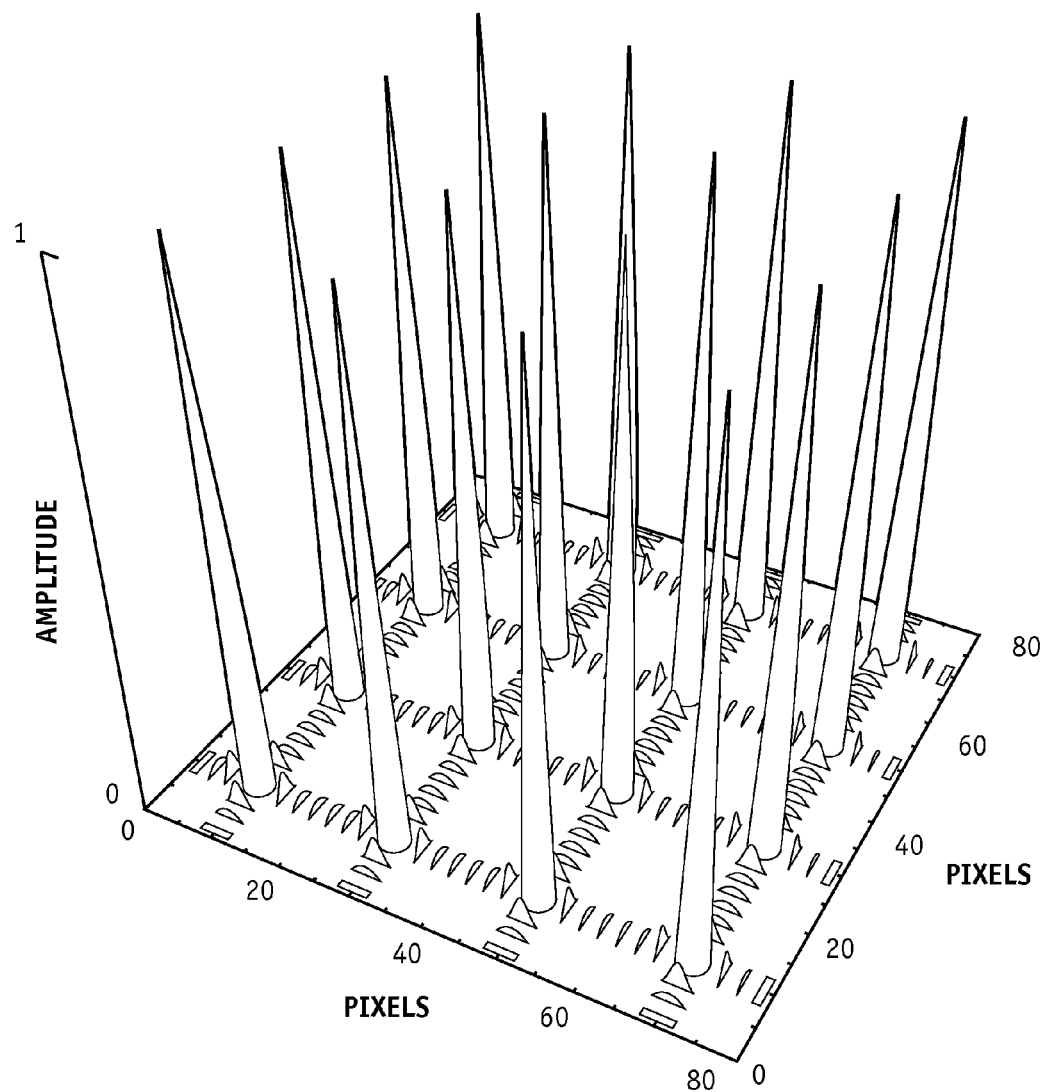
FIGS. 2A-2E illustrate a reference beam and a wavefront of interest being imaged onto a detector array of a wavefront sensor.
Figure 2B:
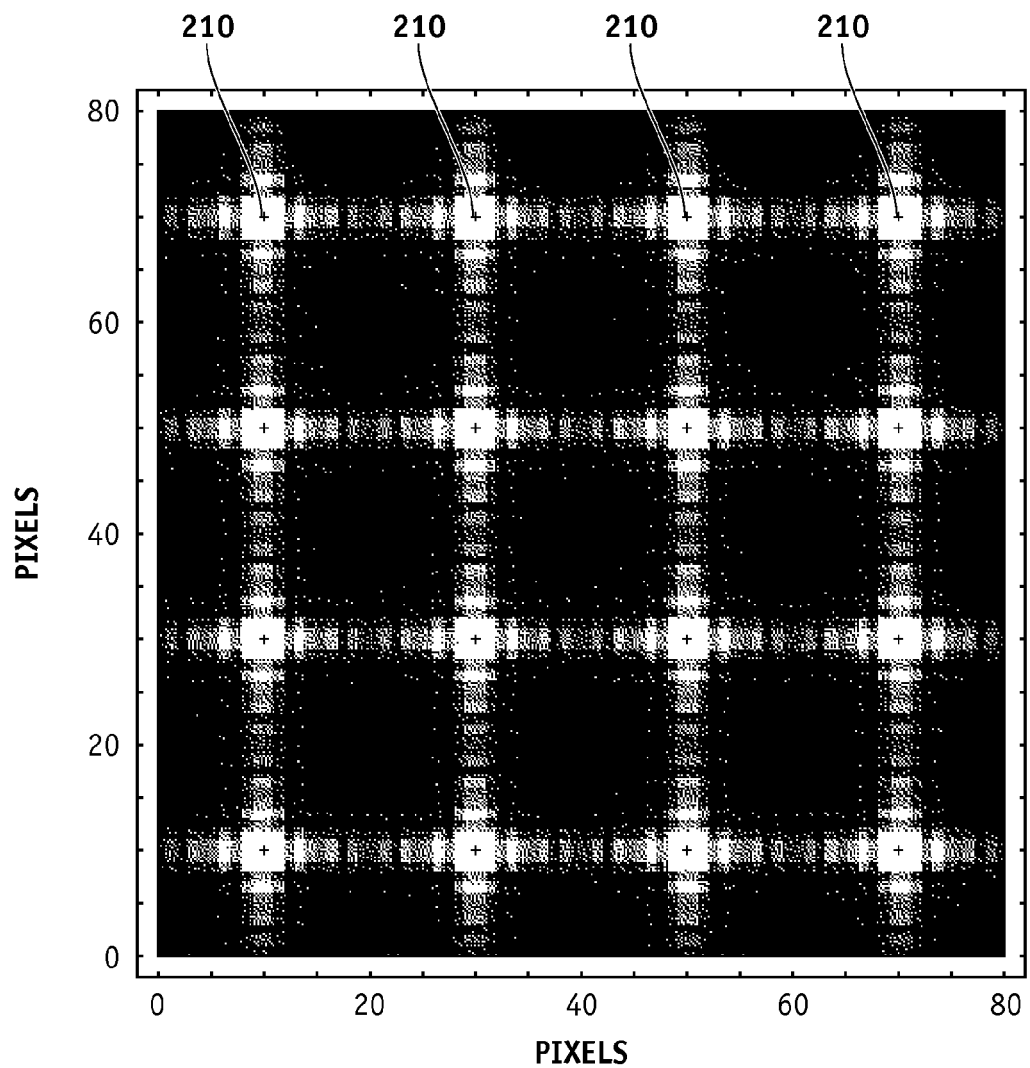
Figure 2C:
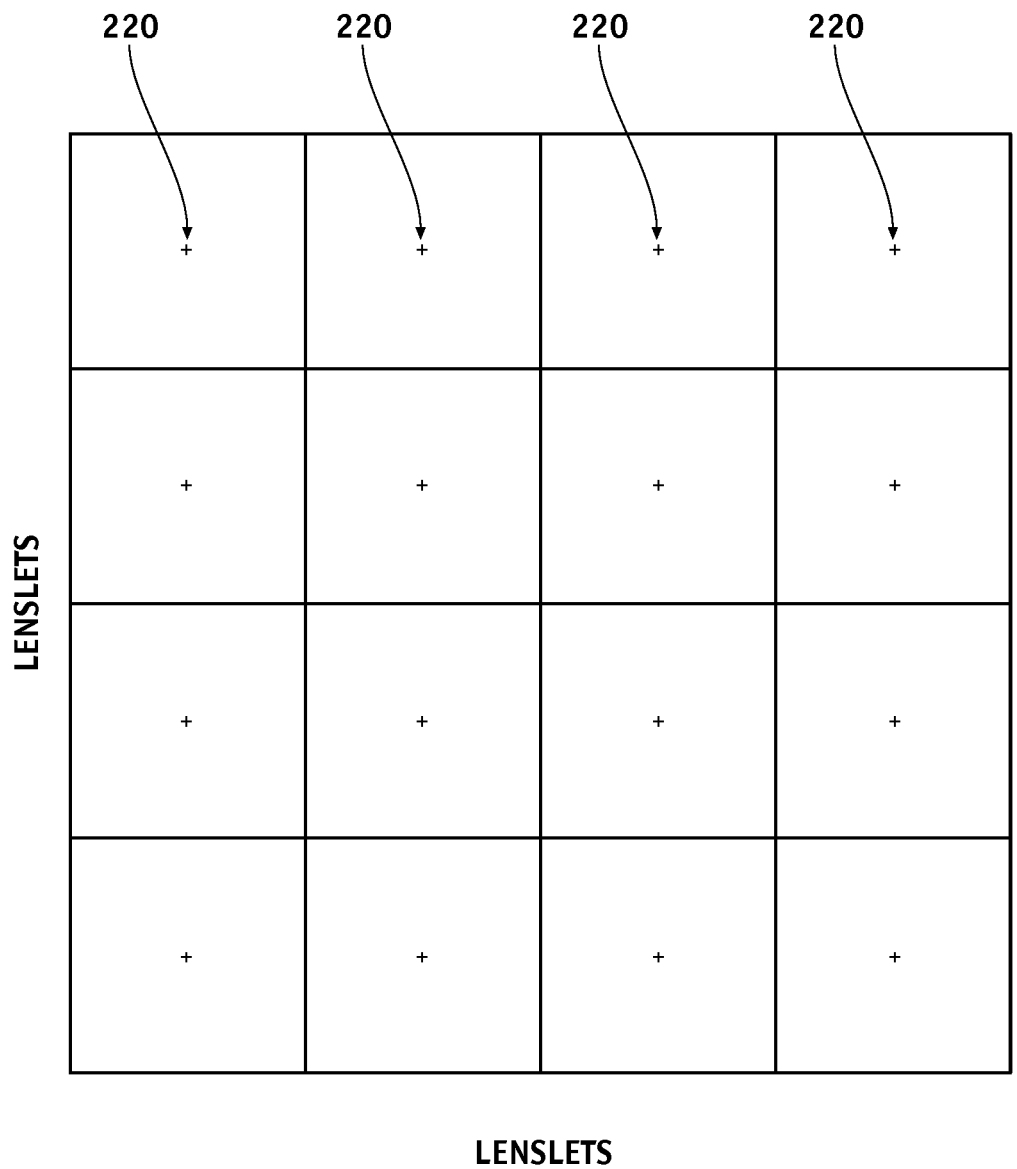
Figure 2D:
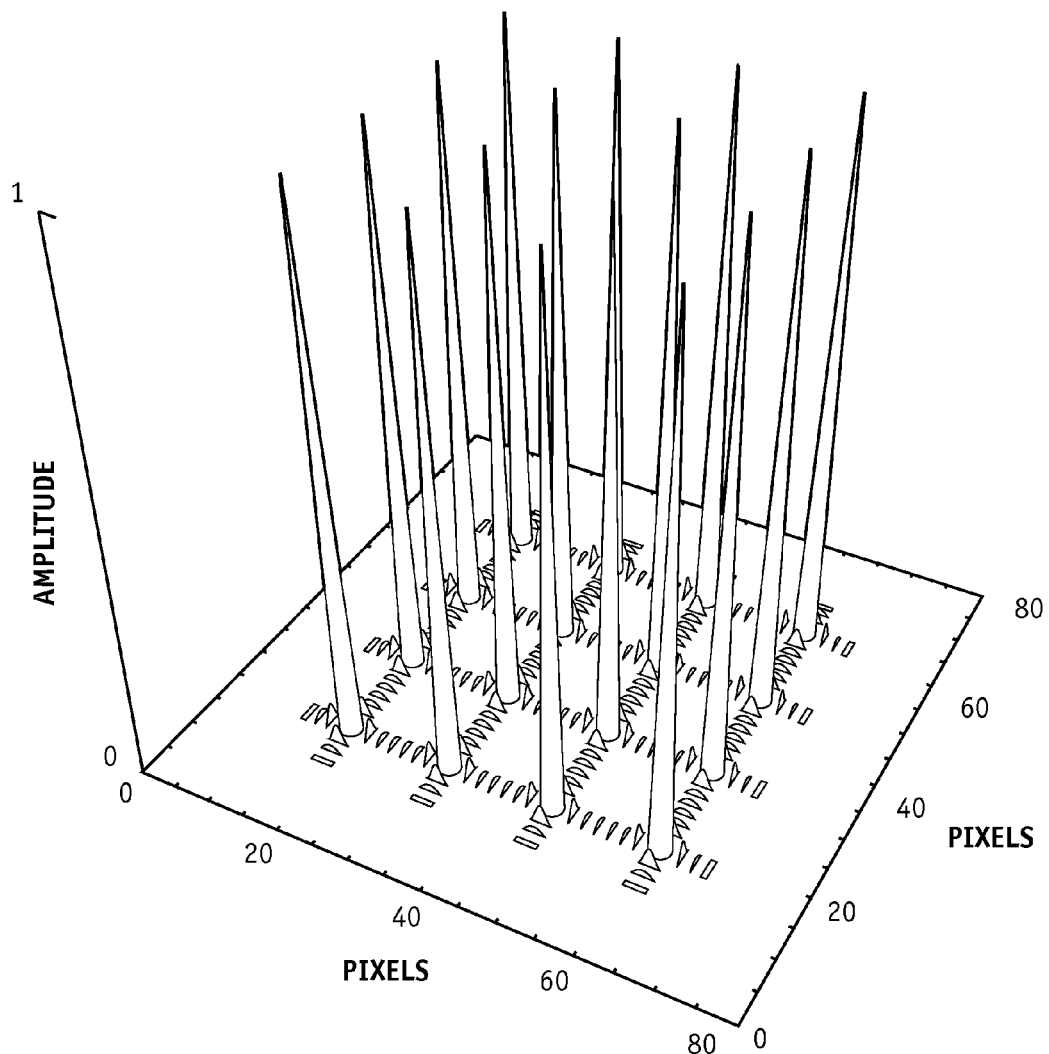
Figure 2E:
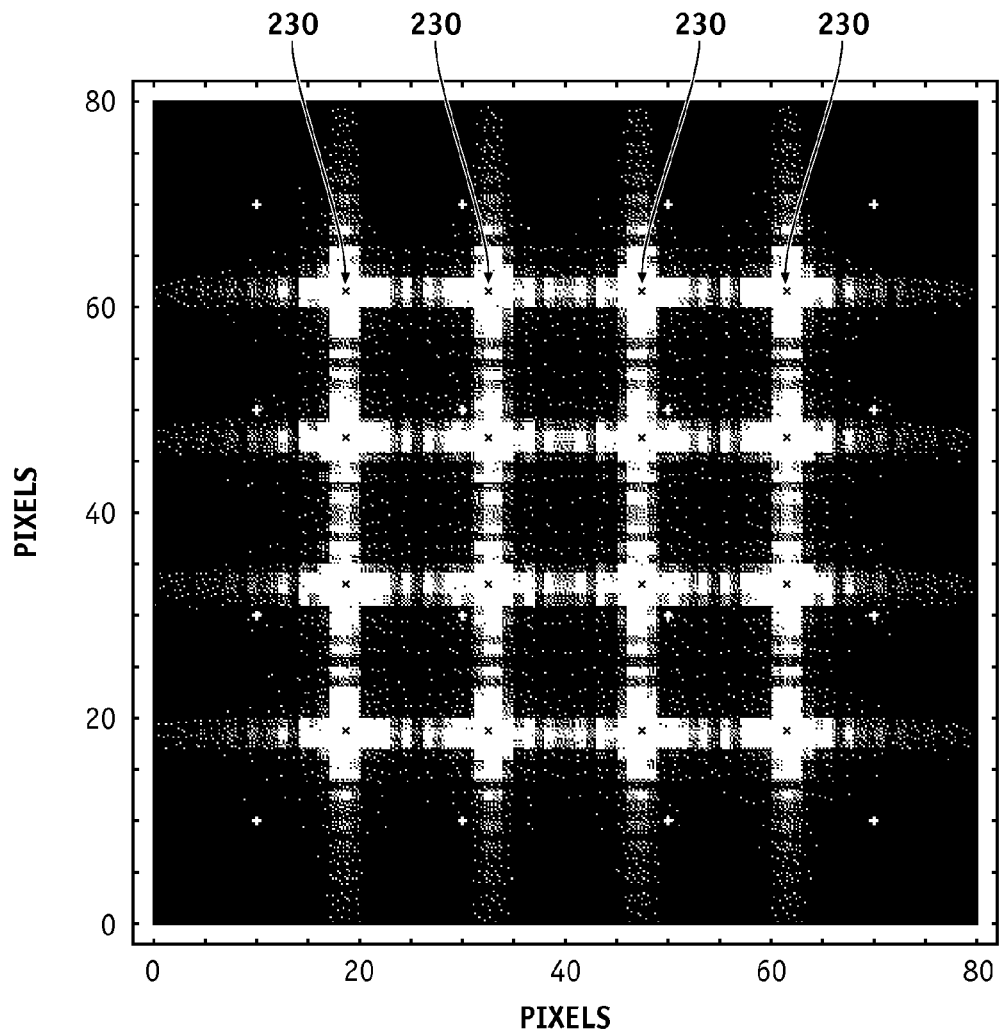
Figure 3:
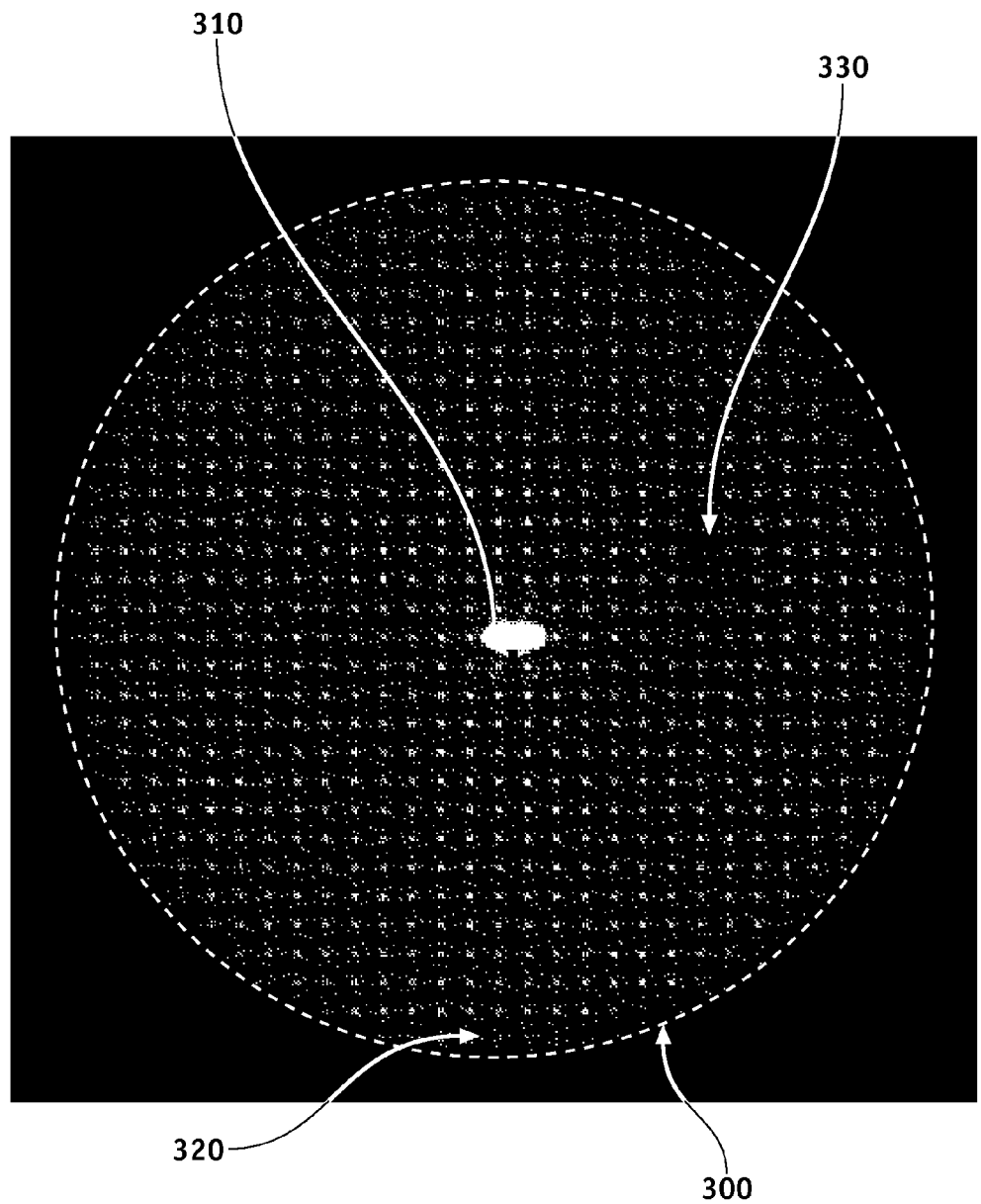
FIG. 3 illustrates the locations of light spots produced by imaging onto a detector array of a wavefront sensor a non-planar wavefront of interest.

Of particular relevance here, wavefront sensor 420 operates in conjunction with processor 440 and associated memory 450 to perform wavefront measurements on eye 10. Wavefront sensor 420 includes a lenslet array 422 and a detector array (also known as a "pixel array") 424. Further details of the construction and operation of lenslet array 422 and detector array 424 may be understood with reference to the description of wavefront sensor 100 of FIG. 1 provided above. Light spot data from detector array 424 is supplied to processor 440 and associated memory 450 to execute one or more algorithms to determine a wavefront of a light beam received from the eye 10. Beneficially, processor 440 may perform these algorithms in accordance with instructions stored in memory 450.

Beneficially, processor 440 executes an algorithm to determine the locations of light spots on detector array 424.

Figure 5:
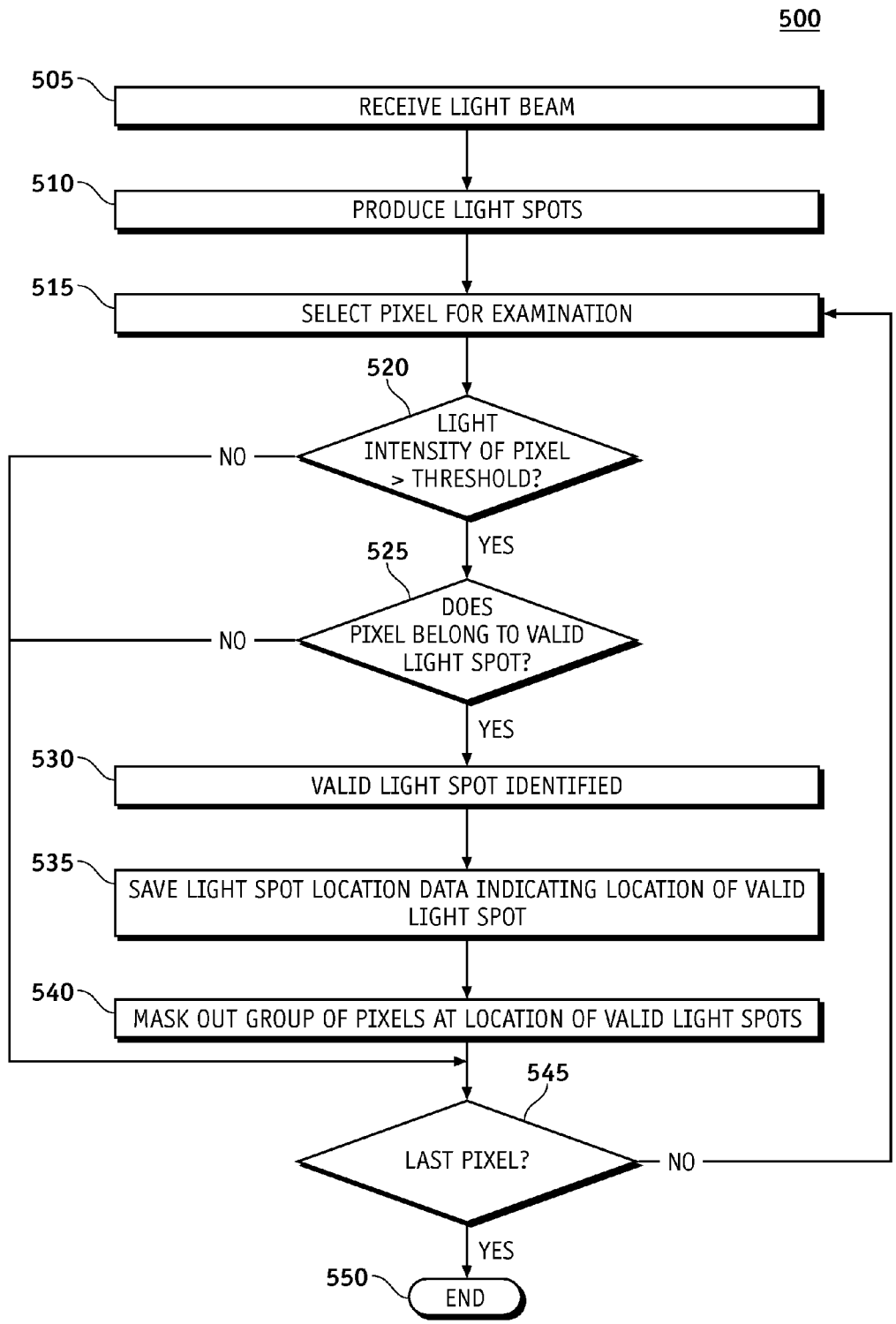
FIG. 5 shows a flowchart illustrating one embodiment of a method of determining the locations of valid light spots among an array of pixel data produced from a wavefront measurement.

FIG. 5 shows a flowchart illustrating one embodiment of a method 500 of determining the locations of valid light spots among an array of pixel data produced from a wavefront measurement. Beneficially, in one embodiment method 500 may be performed by wavefront aberrometer 400 under control of processor 440. Accordingly, to provide a more concrete explanation, method 500 will be described below with respect to wavefront aberrometer 400. However, it should be understood that in general method 500 of may be performed by devices other than wavefront aberrometers which produce a plurality of light spots on a detector array, or by wavefront aberrometers having different configurations than wavefront aberrometer 400. For example, the light spots may be produced by a corneal topographer, where light reflected from a cornea or other surface are imaged onto a detector to produce a set of light spots that are indicative of a local slope of the cornea or surface. In one embodiment method 500 may be performed by a system such as the system 1000 which will be described in greater detail below with respect to FIG. 10.

In an act 505, wavefront aberrometer 400 receives a reflected or diffracted light beam from an object of interest, for example from a calibration object or an object under test (e.g., human eye 10 in FIG. 4).

In an act 510, wavefront aberrometer 400 produces from the received light beam a plurality of light spots on detector array 424. In particular, lenslet array 422 receives the light beam and produces therefrom a plurality of light spots on detector array 424. The locations of these light spots reflect aberrations of the received light beam produced by the object of interest and can be used to determine one or more characteristics of interest of the object of interest.

In an act 515, a pixel of detector array 424 is selected for examination to determine whether it might be included in the pixels illuminated by one of the light spots from lenslet 422. Act 515 is one act in a process of scanning or looping through the pixels of detector array 424 one by one to search for the locations of all of the light spots produced by lenslet array 422. In a beneficial embodiment of method 500, processor 440 sequentially loops through the pixels one by one, examining the pixel data for each pixel until all of the pixels of detector array 424 have been examined. In a particular beneficial embodiment of method 500, processor 440 may begin the looping process at a corner pixel of pixel array 424 (e.g., an "upper left corner" pixel, and advance horizontally or vertically to the next pixel until all pixels of the first column or row are examined, then proceed to the next row or column, etc, until all pixels of pixel array 424 have been examined.

In an act 520, processor 440 compares the light intensity detected by the selected pixel with a predefined threshold to determine whether the pixel might belong to a valid light spot on detector array 424. In particular, processor 440 may compare a light intensity value of the pixel data of the selected pixel with a predefined threshold, $T_A$. Beneficially, the predefined threshold $T_A$ may be selected such that only a pixel that is located close to a pixel whose light intensity value is the maximum for a particular light spot will have a light intensity value that is greater than the threshold $T_A$. Selecting a value for the predefined threshold $T_A$ that is near to the expected maximum light intensity value for a light spot can expedite the process of determining the locations of the light spots on detector array 424, for example by allowing the use of a reduced Area of Interest (AOI) in a light spot validation process 600 which is described below with respect to FIGS. 6A-C.

If it is determined in step 520 that the light intensity value for the selected pixel is not greater than the predefined threshold $T_A$, then the process proceeds to step 545 described below. Otherwise, if it is determined in step 520 that the light intensity value for the selected pixel is greater than the predefined threshold $T_A$, then the process proceeds to step 525.

In an act 525, processor 440 determines whether the selected pixel whose light intensity value is greater than the predefined threshold $T_A$ belongs to a valid light spot. An example embodiment of a method of validating the presence of a light spot which may be employed for act 525 of method 500 will be described in detail below with respect to FIGS. 6A-C.

If it is determined in step 525 that the selected pixel whose light intensity value is greater than the predefined threshold $T_A$ does not belong to a valid light spot, then the process proceeds to step 545 described below. Otherwise, if it is determined in step 525 that the selected pixel whose light intensity value is greater than the predefined threshold $T_A$ belongs to a valid light spot, then in step 530 it is determined that a valid light spot has been identified.

Then in a step 535, processor 440 saves light spot location data identifying a location of the valid light spot on detector array 424. In some embodiments, the light spot location data may identify the pixel whose light intensity value is the maximum among the pixels for the particular light spot. In other embodiments, the light spot location data may identify the location of a centroid of the light spot.

In an act 540, processor 440 masks out a group of pixels of detector array 424 at the location of the valid light spot. Masking out the group of pixels means assigning the pixels each a light intensity value that is less than the threshold $T_A$, for example zero. Accordingly, when pixels in this group of pixels are subsequently selected and their light intensity values are compared against the predefined threshold $T_A$ in step 520 as processor 440 loops through all of the pixels of the detector array 424 for a remainder of the process, processor 440 will determine that the light intensity values for the pixels in the group are not greater than the predefined threshold $T_A$.

Beneficially, in some embodiments processor 440 may mask out a group of pixels corresponding to an expected size of a valid light spot on detector array 424, or corresponding to an expected size of a valid light spot on detector array 424 plus one pixel in each direction. The number of pixels corresponding to the expected size of a valid light spot on the pixel array may be determined by various parameters of wavefront aberrometer 400, particularly the relationship between the size of the lenslets of lenslet array 422 and the size of the pixels of detector array 424. Also beneficially, in some embodiments the group of pixels which are masked out may be centered or approximately centered around the determined location of the light spot (e.g., around the pixel whose light intensity value is the maximum among the pixels for the particular light spot; around the location of a centroid of the light spot; etc.).

In an act 545, processor 440 determines whether or not the previously selected pixel is the last pixel if detector array 424 to be scanned or looped through the process. If so, the process ends at 550. Otherwise, if the previously selected pixel is not the last pixel if detector array 424 to be scanned or looped through the process, then the process returns to act 515 where processor 440 selects a next pixel of detector array 424 for examination.

As described above, in act 525 if processor 440 determines whether or not the selected pixel whose light intensity value is greater than the predefined threshold $T_A$ belongs to a valid light spot. In act 525, beneficially processor 440 executes an algorithm to apply certain validation criteria to light spot data from detector array 424 to validate light spots that satisfy the validation criteria, and to exclude light spots that do not meet the validation criteria. Through such an algorithm, processor 440 may exclude light spots that are of dubious quality, such as light spots near the corneal reflex, light spots that highly saturate detector array 424, and light spots that are distorted by cataracts, tear film breakup, or other ocular conditions.

In a particular embodiment, processor 440 validates light spots produced by lenslet array 422 and a detector array 424 by performing one or more tests to determine whether the light spot data is believed to have been influenced by extraneous factors such as: corneal reflex: cataracts, "floaters" and opaque regions in the eye; intraocular lenses, tear film breakup; etc. Therefore, beneficially, wavefront aberromoter 400 may exclude such light spots from the set of light spots used for calculating the received wavefront, FIGS. 6A-C are flowcharts illustrating one embodiment of a method of validating a potential light spot on a pixel array.

Figure 6A:
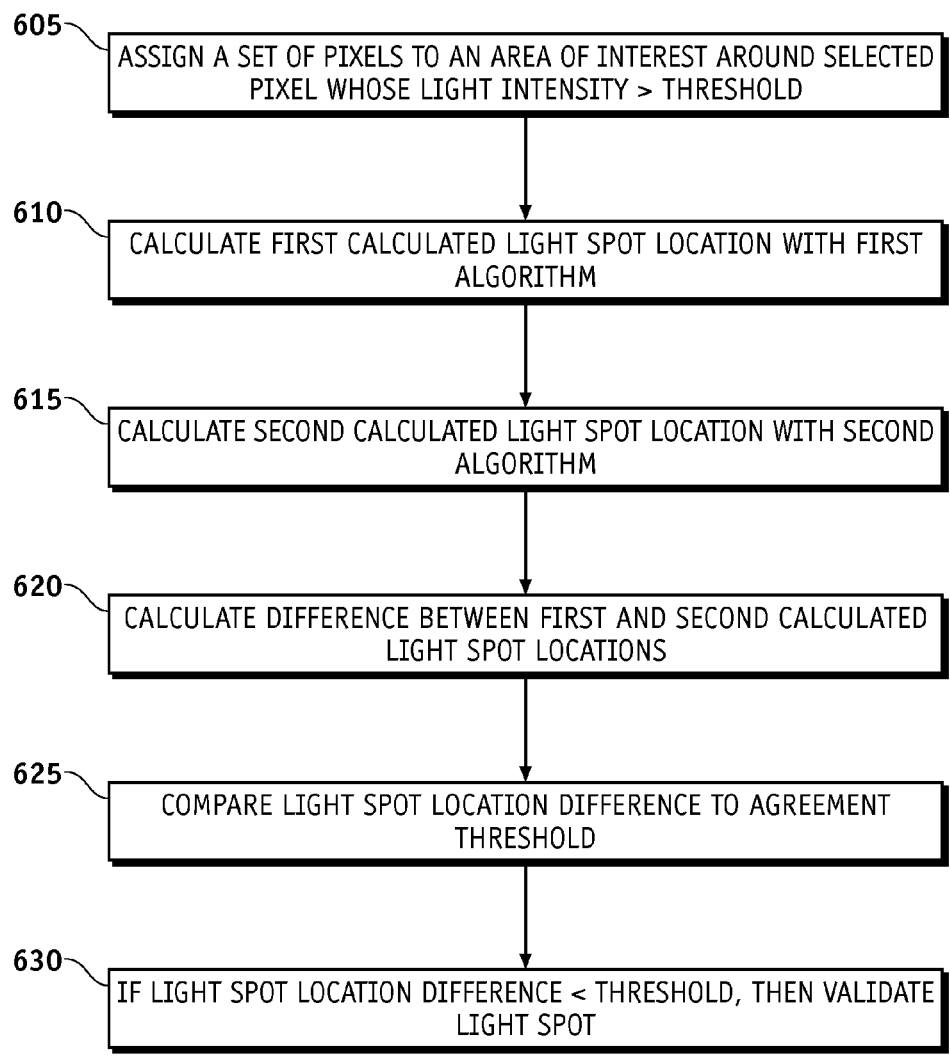
FIGS. 6A-C are flowcharts illustrating one embodiment of a method of validating a potential light spot on a pixel array.
Figure 6B:
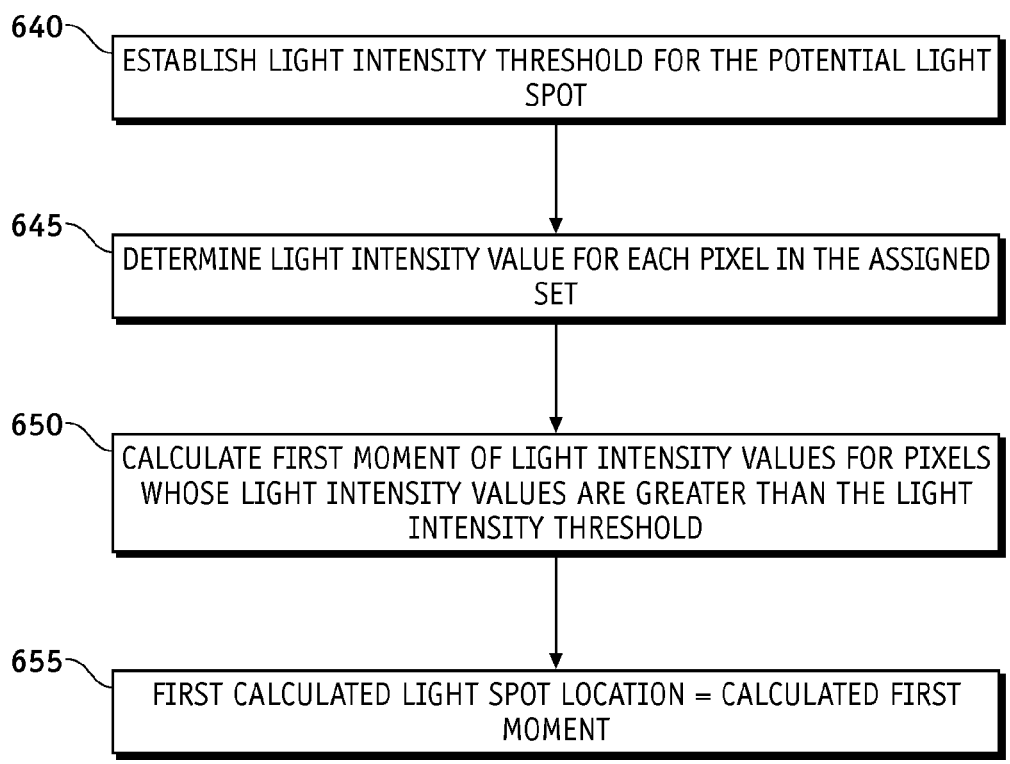
Figure 6C:
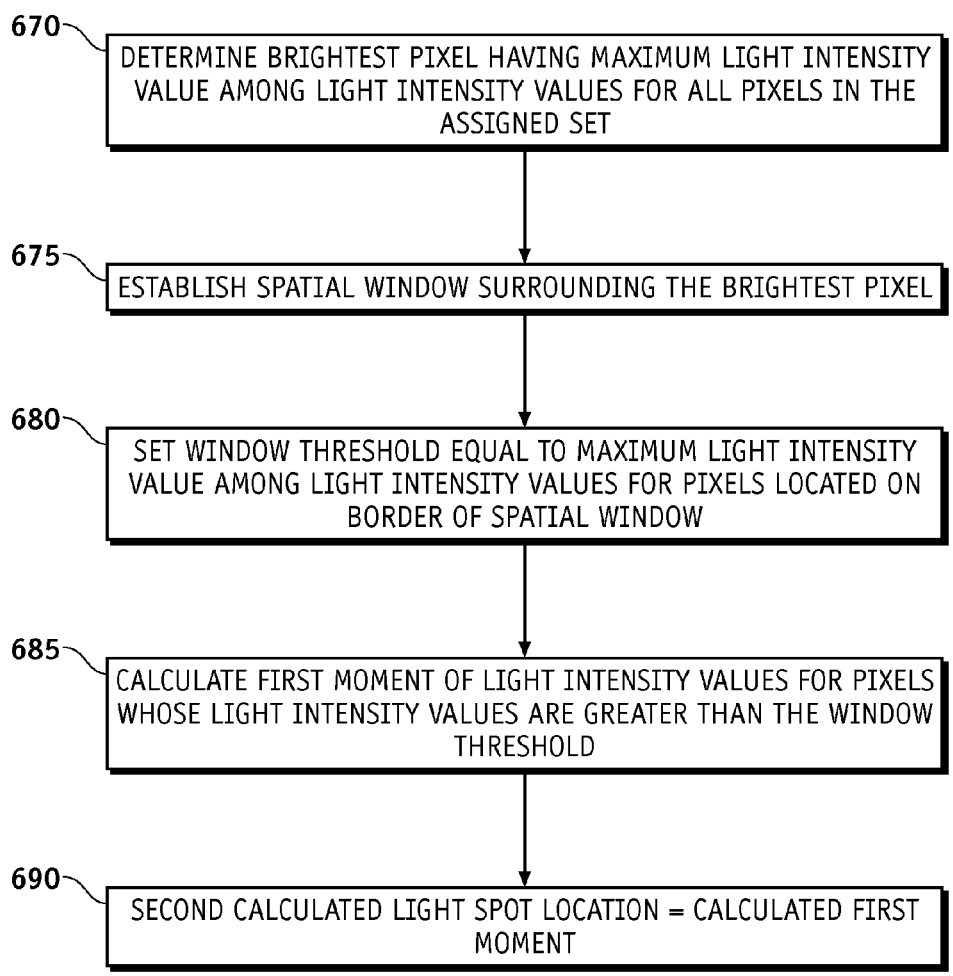

In particular, FIGS. 6A-C are flowcharts illustrating one embodiment of a method of determining whether a selected pixel whose light intensity value is greater than the predefined threshold $T_A$ belongs to a valid light spot, such as may be employed in act 525 of method 500.

As shown in FIG. 6A, in an act 605 processor 440 assigns a set of pixels to an Area of Interest (AOI) around the selected pixel whose light intensity value is greater than the predefined threshold $T_A$. Beneficially, the number of pixels assigned to the AOI is greater than the number of pixels for an expected size of a valid light spot on detector array 424, which may be determined by various parameters of wavefront aberrometer 400, particularly the relationship between the size of the lenslets of lenslet array 422 and the size of the pixels of detector array 424. For example, in one arrangement where the expected size of a light spot on detector array 424 is 16 pixels, a total of 64 pixels may be assigned to the AOI. Furthermore, the AOI may be centered about the selected pixel whose light intensity value is greater than the predefined threshold $T_A$. Alternatively, in some embodiments where processor 440 scans or loops through the pixels of detector array 424 from an upper left corner of detector array 424 to a lower right corner of detector array 424, the AOI may be skewed to the lower right with respect to the selected pixel whose light intensity value is greater than the predefined threshold $T_A$.

In general, there is a relationship between the predefined threshold $T_A$ that is selected, and the number of pixels that are assigned to the AOI. For example, if the predefined threshold $T_A$ is selected to be greater, then the size of the AOI may be reduced. However there is a limit in that the predefined threshold $T_A$ should not be selected to be so great that a valid light spot is possibly missed, and the AOI should not be selected to be so small that a portion of a valid light spot is not included within the AOI which would possibly lead to the valid light spot being erroneously determined to be invalid in acts 610-630 described below.

In an act 610, processor 440 calculates a first calculated location for a potential light spot within the AOI by employing a first light spot location algorithm. Beneficially, processor 440 calculates a first calculated location for a potential light spot within the AOI by calculating a centroid for the light spot intensity data of detector array 424 within the AOI by employing a first centroid calculation algorithm. One embodiment of a first light spot location algorithm is described below with respect to FIG. 6B.

In an act 615, processor 440 calculates a second calculated location for a potential light spot within the AOI by employing a second light spot location algorithm that is different from the first light spot location data employed in act 610. Beneficially, processor 440 calculates a second calculated location for the potential light spot within the AOI by calculating a centroid for the light spot intensity data of detector array 424 within the AOI by employing a second centroid calculation algorithm that is different than the first centroid calculation algorithm. One embodiment of a second light spot location algorithm is described below with respect to FIG. 6C.

In an act 620, processor 440 calculates a location difference $\Delta_L$ between the first calculated location for the potential light spot of act 610 and the second calculated location for the potential light spot of act 615. For example, the location difference $\Delta_L$ between the first calculated location and the second calculated location may be expressed in terms of a number of, or fraction of, pixels.

In an act 625, processor 440 compares the location difference $\Delta_L$ to a defined location agreement threshold $T_L$. Beneficially, the agreement threshold $T_L$ is selected such that a valid light spot will have a location difference $\Delta_L$ that is significantly less than the defined location agreement threshold $T_L$, while light intensity distributions within an AOI that are not produced by a valid light spot will yield a location difference $\Delta_L$ that is significantly greater than the agreement threshold $T_L$. In some embodiments, the agreement threshold $T_L$ may be selected to be one pixel. In some embodiments, the agreement threshold $T_L$ may be selected to be one pixel.

In an act 630, if location difference $\Delta_L$ is less than the defined location agreement threshold $T_L$, then processor 440 determines that a valid light spot has been found to which the selected pixel whose light intensity value is greater than the predefined threshold $T_A$ belongs. Otherwise, processor 440 determines that there is no valid light spot has been found within the AOI.

FIGS. 6B illustrates one embodiment of a method 635 of calculating a first calculated location of a potential light spot in a method such as method 600 illustrated in FIG. 6A. The method illustrated in FIG. 6B is hereinafter referred to as the "Percent Threshold Method."

The Percent Threshold Method incorporates two parameters: an Irradiance Threshold $T_I$ and a Percent Threshold $T_P$.

The Irradiance Threshold $T_I$ may be used to eliminate camera noise and stray light from the data used in the light spot centroid location calculation and is assumed to be constant across the image. In one embodiment, the Irradiance Threshold $T_P$ may be nominally set at a value of 30 counts from those pixels of the detector array assigned to the AOI.

The Percent Threshold $T_P$ is used to dynamically threshold the intensity data in proportion to the valid data brightness within the AOI to afford a wide variance in the spot brightness. This is in effect a local threshold that depends on the spot brightness that is crucial for use in instruments where a large variance is in spot brightness or size can be expected; e.g., ophthalmic aberrometers and laser metrology tools. It is generally quite robust against spot brightness but assumes a constant background level, the Irradiance Threshold 610.

The raw intensity values of the pixels within a given AOI are thresholded with a value Pixel Intensity Threshold $T_{PI}$ equal to the Irradiance Threshold $T_I$ plus the product of the Percent Threshold $T_P$ times the brightest intensity minus the Irradiance Threshold $T_I$. The x and y first moments of the pixel data within the AOI are then calculated, as is the sum of the valid intensity, i.e., the sum of the raw intensity values minus the Irradiance Threshold $T_I$.

Accordingly, in one embodiment a first method 635 of locating a light spot comprises: an act 640 of processor 440 establishing a pixel intensity threshold for the light spot; an act 645 of determining a light intensity value for light received at each pixel in the AOI; an act 650 of processor 440 calculating a first moment of the light intensity values for those pixels whose light intensity values are greater than the pixel intensity threshold $T_{PI}$; and an act 655 of assigning the calculated first moment as the first calculated location of a potential light spot in the AOI. Furthermore, as described above, in one embodiment, the pixel intensity threshold for the light spot is established by: establishing a background intensity threshold value that is constant for all light spots; determining a maximum intensity value among the intensity values for all of the pixels in the group; establishing a percentage threshold value for the light spot; and establishing the pixel intensity threshold by multiplying the percentage threshold value by the maximum intensity value and subtracting the background intensity threshold value.

FIG. 6C illustrates one embodiment of a method 660 of calculating a first calculated location of a potential light spot in a method such as method 600 illustrated in FIG. 6A. The method illustrated in FIG. 6C is hereinafter referred to as the "Window Method."

The Window Method uses a priori information about the light spot dimensions and the location of the brightest pixel within the AOI to determine which pixels to use in the first moment's calculations, and what background value of light to subtract. In contrast to the Percent Threshold Method which uses local intensity criteria to determine which pixels to include in the first moments calculation, the Window Method uses a spatial criteria and a local background value.

In the Window Method, the raw intensity values of the pixels within a given AOI are reviewed to find the brightest pixel, and a window having predetermined dimensions is centered on the brightest pixel. In a beneficial embodiment, the window is a square whose size is sufficiently large to enclose only the primary lobe of the light spot pattern, but considerably smaller than the AOI. For example, in one arrangement where the AOI includes 65 pixels, the window may be set to four (4) pixels in each direction. In one embodiment, if the brightest pixel in the AOI is located within one half of the window's length from the edge of the AOI, then the window is truncated at the edge of the AOI. Only pixels within window are used to determine the potential light spot's location. The light intensity values of the pixels along the border of the window are reviewed and the brightest value is used to threshold the intensity of the pixels within window with a window threshold $T_W$. Then the x and y first moments and the sum of the thresholded intensity values for pixels in window are calculated.

Significantly, the Window Method returns a light spot location and intensity of zero whenever the intensity of a pixel on the border of window is equal to the intensity of the brightest pixel in the AOI. This routinely occurs in and around the corneal reflex.

Accordingly, in one embodiment a second method 660 of locating a light spot comprises: an act 670 of processor 440 determining the brightest pixel having the maximum light intensity value among the pixels in the AOI; an act 675 of establishing a spatial window surrounding the pixel having the maximum light intensity value among the pixels in the AOI; an act 680 of processor 440 setting a window threshold $T_W$ equal to a maximum light intensity value among the light intensity values for those pixels located on the border of the spatial window; an act 685 of processor 440 calculating a first moment of the light intensity values for those pixels whose light intensity values are greater than the window threshold $T_W$; and an act 690 of assigning the calculated first moment as the second calculated location of a potential light spot in the AOI.

As described above, FIGS. 6A-C illustrate one embodiment of a method of determining whether a selected pixel whose light intensity value is greater than predefined threshold $T_A$ belongs to a valid light spot. However other methods are possible. For example, in another example embodiment, processor 440 may calculate a correlation score between an ideal light spot and measured pixel data within a defined area of interest (AOI) with respect to the selected pixel whose light intensity value is greater than the predefined threshold $T_A$. Processor 440 may compare the correlation score to a correlation threshold $T_C$ to validate the light spot, and also to locate a centroid of the light spot which may be saved as location data for the light spot. In some embodiment, the above-described algorithm may be employed in act 525 of method 500.

Figure 7A:
FIGS. 7A-E illustrate various stages of a process of locating valid light spots among an array of pixel data produced from a wavefront measurement.
Figure 7B:
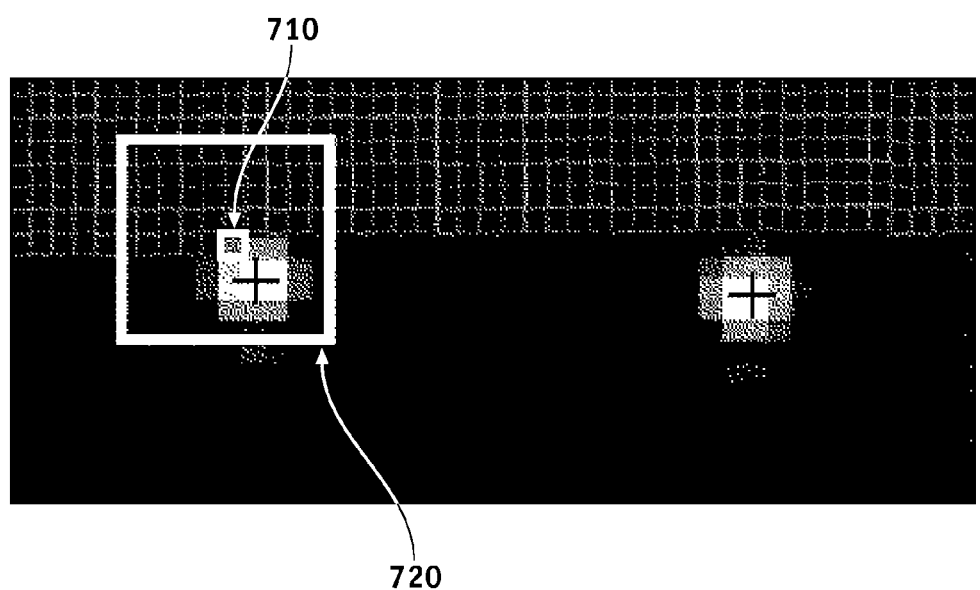
Figure 7C:
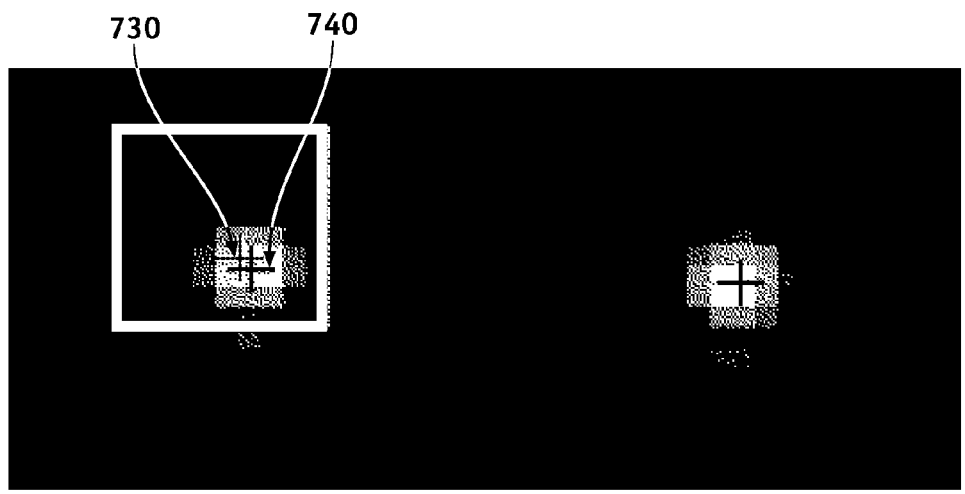
Figure 7D:
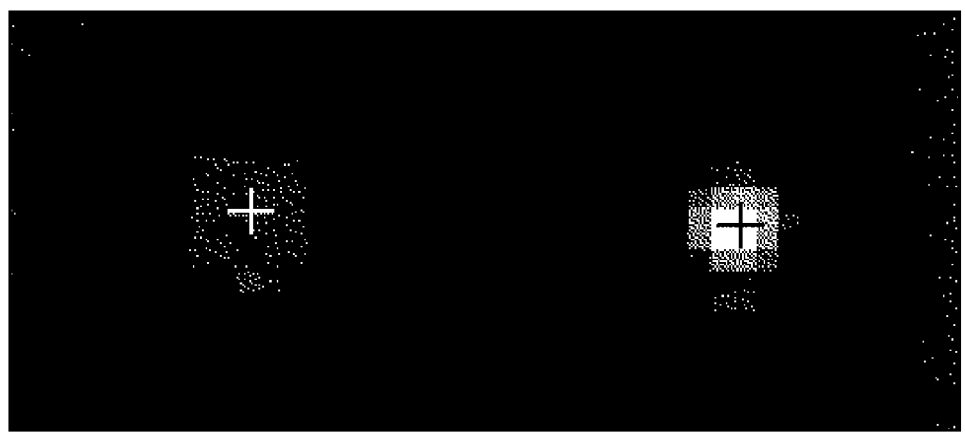
Figure 7E:
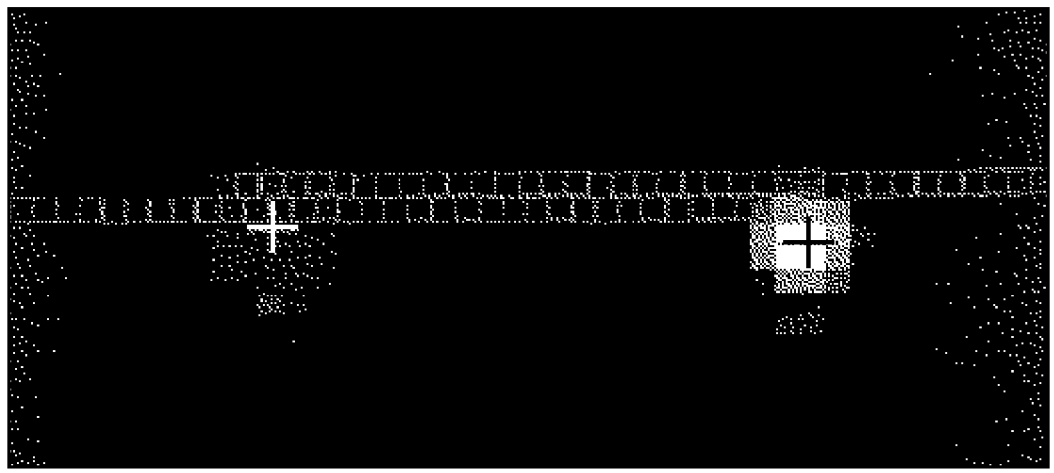

FIGS. 7A-E illustrate various stages of a process of locating valid light spots among an array of pixel data produced from a wavefront measurement, such as the process described above with respect to FIG. 5. In particular, FIG. 7A illustrates scanning or looping through selected pixels of detector array 424 beginning at an upper left corner of detector array 424 by repeating the loop of steps 515, 520 and 545. FIG. 7B illustrates examining a selected pixel 710, identified by the small square in FIG. 7B, whose light intensity value is greater than the predefined threshold $T_A$, and assigning a set of pixels to an Area of Interest (AOI) 720, identified by the large square in FIG. 7B, about the selected pixel 710. FIG. 7C illustrates a process of determining whether or not selected pixel 710 belongs to a valid light spot by calculating potential light spot locations 730 and 740 within AOI 720 by two different methods or algorithms. FIG. 7D illustrates a process of masking out a group of pixels about the location of the validated light spot. FIG. 7E illustrates continuing the process of scanning or looping through selected pixels of detector array 424 beginning at the next pixel of detector array 424 by repeating the loop of steps 515, 520 and 545, where the group of pixels around the previously-validated light spot have been masked out.

Figure 8A:
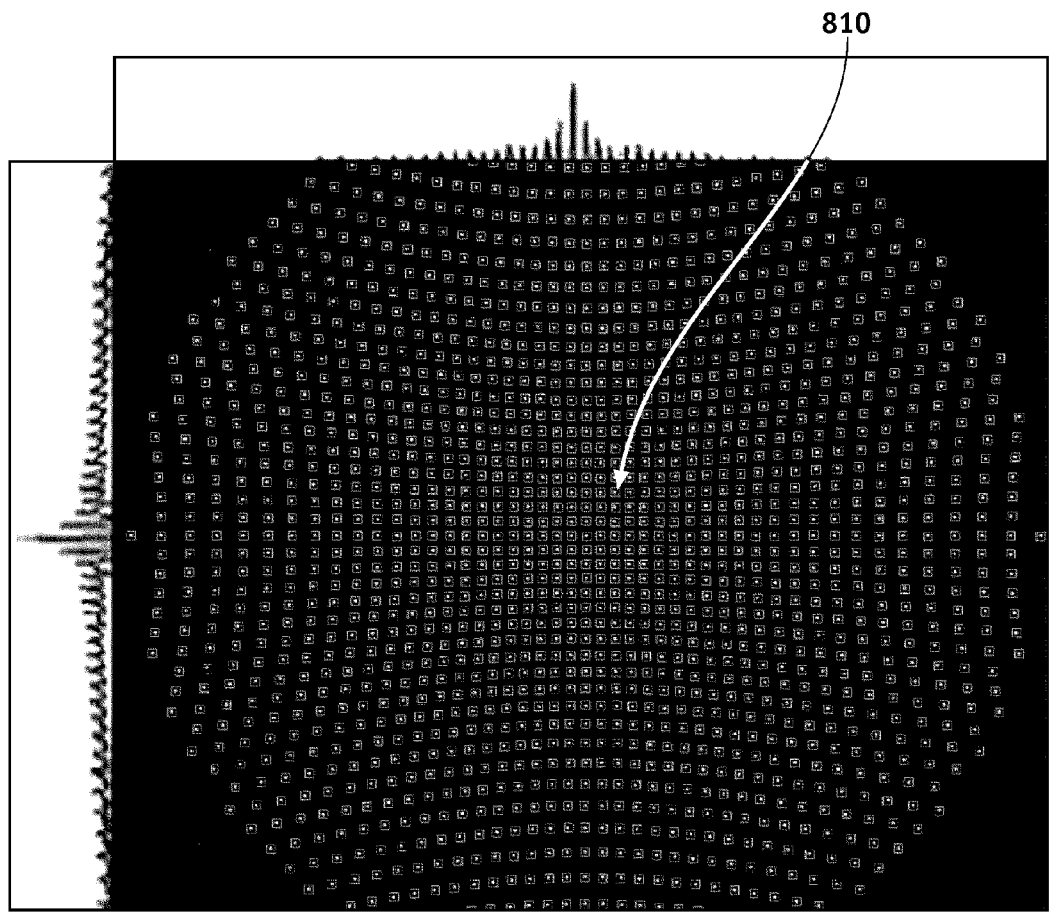
FIGS. 8A-B illustrate an example of a light spot pattern produced by a method and system that assigns fixed areas-of-interest for each light spot.
Figure 8B:
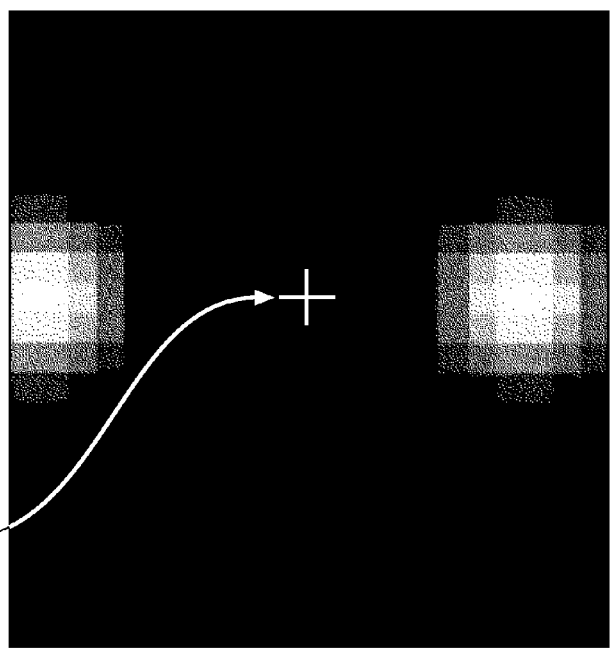

FIGS. 8A-B illustrate an example of a light spot pattern produced by a method and system that assigns fixed areas-of-interest (AOIs) for each light spot, such as may be employed in a conventional wavefront aberrometer. In particular, FIGS. 8A-B illustrate how using fixed AOIs causes an error in this case whereby two light spots are present within one AOI.

Figure 9:
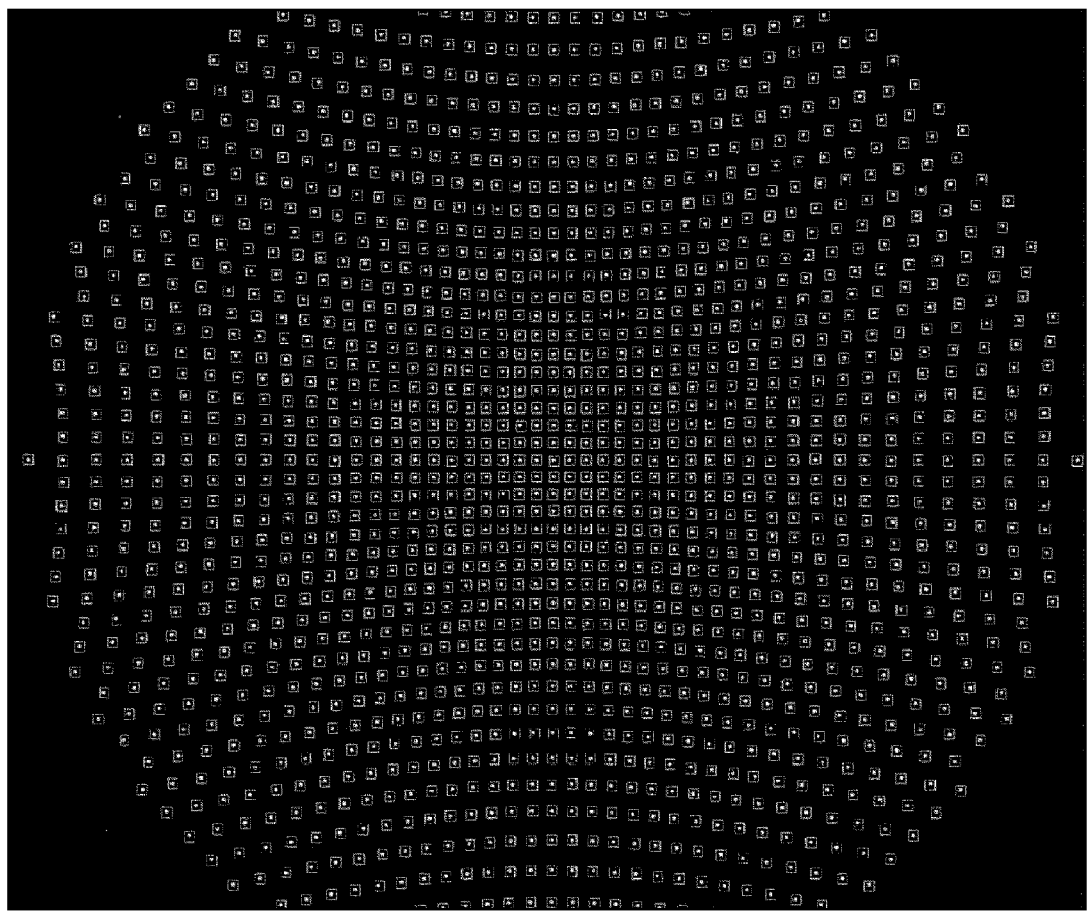
FIG. 9 illustrates an example of a light spot pattern produced by a method and system as illustrated with respect to FIG. 5.

FIG. 9 illustrates an example of a light spot pattern produced by a method and system as illustrated with respect to FIGS. 5 and 6A-C. The example light spot pattern of FIG. 9 is produced from the same pixel data as the light spot pattern of FIGS. 8A-B. However, the example light spot pattern of FIG. 9 employs sliding, or dynamically-assigned, AOIs as explained above with respect to FIGS. 5 and 6A-C, and accordingly it avoids placing two light pots within the same AOI as each other.

Figure 10:
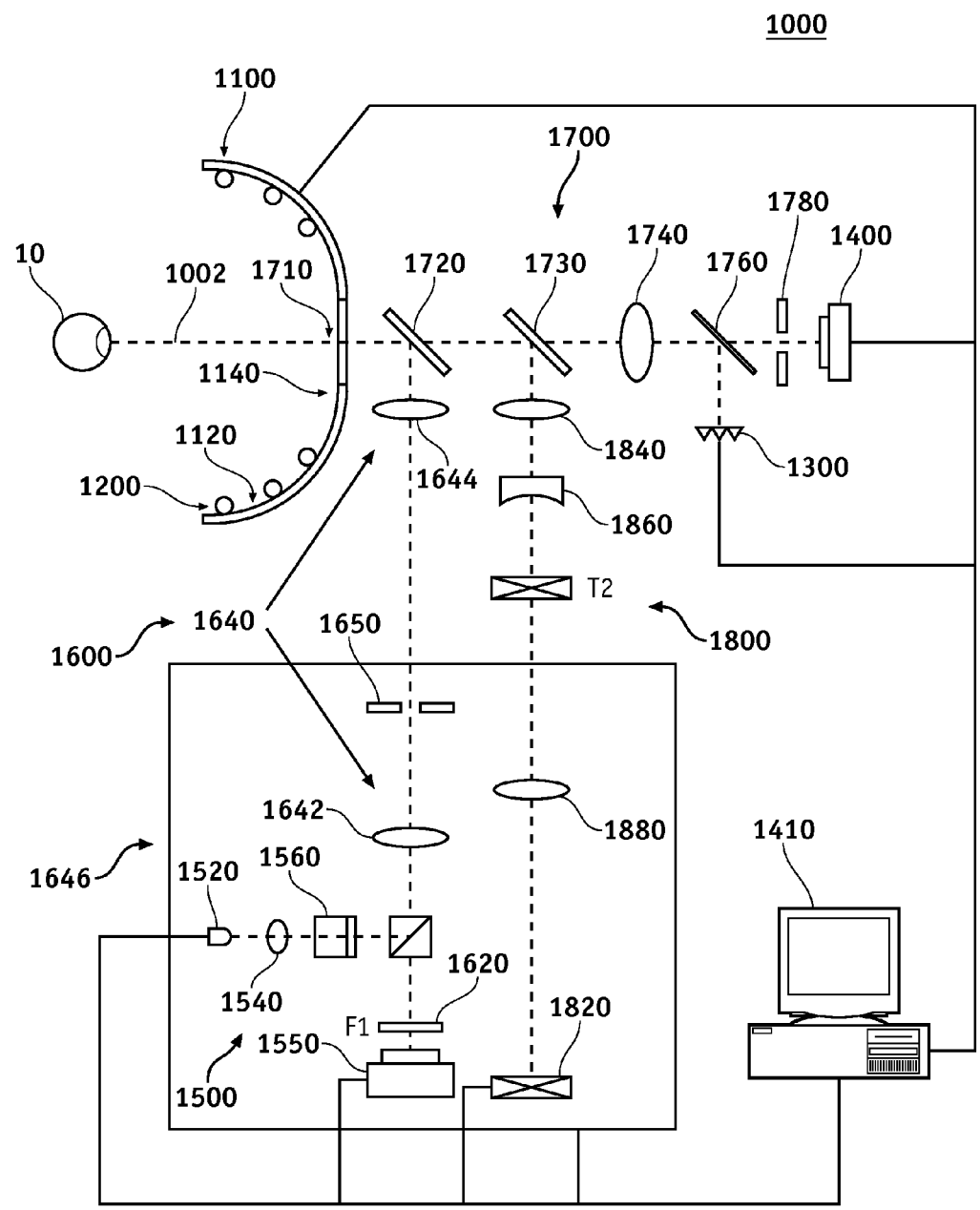
FIG. 10 illustrates one embodiment of a system for measuring wavefront aberrations and corneal topography of an eye.

FIG. 10 shows one embodiment of a system 1000 for measuring aberrations and the corneal topography of an eye 10. System 1000 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); a detector array 1400; a processor 1410; a third light source 1500 providing a probe beam; a wavefront sensor 1550; and an optical system 1700 disposed along a central axis 1002 passing through the opening or aperture 1140 of the structure 1100. Optical system 1700 comprises a quarterwave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element. Beneficially, system 1000 further comprises a fixation target system 1800, comprising light source 1820 and lenses 1840, 1860, and 1880.

Further details of system 1000 can be found by reference to U.S. Patent Application Publication 2009/0002631, filed in the names of Charles E. Campbell et al., and published on 1 Jan. 2009, the entirety of which is hereby incorporated herein by reference for all purposes as if fully set forth herein.

The operation of the topographer portion of system 1000 may be illustrated based on the combined use of first and second light sources 1200, 1300. In general, the images of first light sources 1200 that appear on detector array 1400 emanate from an outer region of the surface of the cornea, and the images of second light sources 1300 that appear on detector array 1400 emanate from a central or paraxial region of the surface of the cornea. Accordingly, even though information about the central region of the corneal surface (e.g., surface curvature) cannot be determined from the images of first light sources 1200 on detector array 1400, such information can be determined from the images of second light sources 1300 on detector array 1400.

Detector array 1400 detects the light spots projected thereon from both second light sources 1300 (detected at a central portion of detector array 1400) and first light sources 1200 (detected at a peripheral portion of detector array 1400) and provides corresponding output signals to processor 1410. Processor 1410 determines the locations and/or shapes of the light spots on detector array 1400, and compares these locations and/or shapes to those expected based for a standard or model cornea, thereby allowing processor 1410 to determine the corneal topography of eye 100. Accordingly, the topography of the entire corneal surface can be characterized by system 1000 without a "hole" or missing data from the central corneal region.

Pixel data from the wavefront sensor 1550 may be analyzed using the method 500 described above.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A method of locating a set of valid light spots produced on a pixel array by a wavefront of interest, the method comprising:
   a first stage, including:
     selecting a pixel of the pixel array;
   a second stage, including:
     determining whether a light intensity value for the selected pixel is greater than a threshold,
     when the light intensity value for the selected pixel is determined to be greater than the threshold, determining whether the selected pixel belongs to a valid light spot, the determining comprising:
       assigning a set of the pixels including the selected pixel as an area of interest for the potential light spot;
       calculating a first calculated location of a centroid of the potential light spot within the area of interest including using a first calculation algorithm;
       calculating a second calculated location of the centroid of the potential light spot within the area of interest using a second calculation algorithm different from the first calculation algorithm; and
       when a difference between the first and second calculated locations of the centroid for the potential light spot is less than an agreement tolerance, determining that the pixel belongs to a valid light spot, and otherwise, determining that the selected pixel does not belong to a valid light spot;
     when the selected pixel is determined to belong to a valid light spot:
       saving light spot location data indicating a determined location for the valid light spot with respect to the pixel array, and
       masking out a group of pixels of the pixel array corresponding to a defined area at the determined location of the valid light spot such that the masked pixels are considered for a remainder of the method to have light intensity values less than the threshold; and
   repeating the first stage and the second stage for a plurality of pixels of the pixel array.

2. The method of claim 1, wherein calculating the first calculated location for the centroid for the potential light spot using the first calculation algorithm comprises:
   establishing a pixel intensity threshold for the potential light spot;
   determining a light intensity value for each pixel in the set; and
   calculating the first calculated location as a first moment of the light intensity values for those pixels whose light intensity values are greater than the pixel intensity threshold.

3. The method of claim 2, wherein establishing the pixel intensity threshold for the potential light spot comprises:
   establishing a background intensity threshold;
   determining a maximum light intensity value among the light intensity values for all of the pixels in the set;
   establishing a percentage threshold value for the potential light spot; and
   establishing the pixel intensity threshold by multiplying the percentage threshold value by the maximum light intensity value, and subtracting the background intensity threshold value.

4. The method of claim 2, wherein calculating the second calculated location for the centroid for the potential light spot using the second calculation algorithm comprises:
   determining a brightest pixel having a maximum light intensity value among the light intensity values for all of the pixels in the set;
   establishing a spatial window surrounding the brightest pixel;
   setting a window threshold equal to the maximum light intensity value among the light intensity values for pixels located on a border of the spatial window; and
   calculating the second calculated location as a first moment of the pixel intensity values for those pixels in the set whose intensity values are greater than the window threshold.

5. The method of claim 3, wherein a number of pixels in the assigned set of the pixels is greater than a number of pixels for an expected size of the valid light spot on the pixel array.

6. The method of claim 5, wherein a number of pixels in the assigned set of the pixels is greater than a number of pixels in the defined area at the determined location.

7. The method of claim 1, wherein the agreement tolerance is one pixel.

8. The method of claim 1, wherein the defined area at the determined location equals an expected size of a valid light spot on the pixel array.

9. The method of claim 1, wherein the defined area at the determined location equals an expected size of a valid light spot on the pixel array, plus one pixel in each direction.

10. The method of claim 1, wherein masking out the group of pixels of the pixel array corresponding to a defined area at the determined location of the valid light spot comprises:
- determining a central pixel for the valid light spot, and
- masking out the group of pixels of the pixel array corresponding to the defined area around the central pixel.

11. A device, comprising:
- a pixel array;
- a light spot generator adapted to receive light from an illuminated objected and to produce a group of light spots on the pixel array from the light received from the illuminated object; and
- a processor adapted to determine locations of the light spots on the pixel array by executing an algorithm comprising:
  - a first stage, comprising:
    - selecting a pixel of the pixel array;
  - a second stage, comprising:
    - determining whether a light intensity value for the selected pixel is greater than a threshold,
    - when the light intensity value for the selected pixel is determined to be greater than the threshold, determining whether the selected pixel belongs to one of the light spots, the determining comprising:
      - assigning a set of the pixels including the selected pixel as an area of interest for the potential light spot;
      - calculating a first calculated location of a centroid of the potential light spot within the area of interest including using a first calculation algorithm;
      - calculating a second calculated location of the centroid of the potential light spot within the area of interest using a second calculation algorithm different from the first calculation algorithm; and
      - when a difference between the first and second calculated locations of the centroid for the potential light spot is less than an agreement tolerance, determining that the pixel belongs to a valid light spot, and otherwise, determining that the selected pixel does not belong to a valid light spot;
    - when the selected pixel is determined to belong to one of the light spots:
      - saving light spot location data indicating a determined location for the one light spot with respect to the pixel array, and
      - masking out a group of pixels of the pixel array corresponding to a defined area at the determined location of the one light spot such that the masked pixels are considered for a remainder of the algorithm to have light intensity values less than the threshold; and
- repeating the first stage and the second stage for a plurality of pixels of the pixel array.

12. The device of claim 11, wherein the light spot generator is a lenslet array.

13. The device of claim 11, further comprising an illumination system for illuminating the illuminated object.

14. The device of claim 11, wherein the illuminated object is an eye, and where the processor is further configured to process the light spot location data to determine an abnormality of the eye.

15. The device of claim 11, wherein the device includes a wavefront aberrometer employing the spot locations to characterize a wavefront of light received from the eye.

16. The device of claim 11, wherein the device includes a corneal topographer employing the spot locations to characterize a corneal topography of an eye.

17. A method, comprising:
- sequentially processing pixels of an image detector, wherein processing a pixel includes determining whether a light intensity detected by the pixel is greater than a threshold;
- when the light intensity detected by the pixel is determined to be greater than the threshold, determining whether the pixel belongs to a valid light spot for measuring a wavefront of interest; and
- when the pixel is determined to belong to a valid light spot:
  - saving data indicating a location for the valid light spot, and
  - masking out a group of pixels of the image detector at the location of the valid light spot such that the masked pixels are considered to have a light intensity less than the threshold for a remainder of the sequential processing of the pixels,
- wherein determining whether the pixel belongs to a valid light spot comprises:
- calculating a first calculated location of a centroid of a potential light spot including using a first calculation algorithm;
- calculating a second calculated location of the centroid of the potential light spot using a second calculation algorithm different from the first calculation algorithm; and
- when a difference between the first and second calculated locations of the centroid for the light spot is greater than an agreement tolerance, determining that the pixel belongs to a valid light spot, and otherwise, determining that the pixel does not belong to a valid light spot.

18. The method of claim 17, further comprising, when the pixel is determined to belong to a valid light spot, determining a location for the valid light spot.

* * * * *